United States Patent
Einerhand et al.

(10) Patent No.: US 6,312,957 B1
(45) Date of Patent: Nov. 6, 2001

(54) GENETIC MODIFICATION OF PRIMATE HEMOPOIETIC REPOPULATING STEM CELLS

(75) Inventors: Markus Peter Wilhelmus Einerhand, Amsterdam; Domenico Valerio, Leiden, both of (NL)

(73) Assignee: Introgene B.V. (NL)

(*) Notice: Subject to any disclaimer, the term of this patent is extended or adjusted under 35 U.S.C. 154(b) by 0 days.

(21) Appl. No.: 09/326,032

(22) Filed: Jun. 4, 1999

Related U.S. Application Data

(63) Continuation of application No. PCT/NL97/00631, filed on Nov. 19, 1997.

(30) Foreign Application Priority Data

Dec. 5, 1996 (EP) .................................................. 96203444

(51) Int. Cl.[7] ........................... C12N 15/864; C12N 15/63
(52) U.S. Cl. ............................................... 435/456; 435/440
(58) Field of Search ....................... 424/93.1; 435/320.1, 435/235.1, 325, 91.1, 91.4, 455, 2, 456, 440; 536/23.5, 24.1

(56) References Cited

FOREIGN PATENT DOCUMENTS

WO 93/09239 * 5/1993 (WO) .
WO 97/00326   1/1997 (WO) .

OTHER PUBLICATIONS

Anderson Nature 392 Suppl:25–30 1998.*
Collis et al. EMBO J. 9:233–240 1990.*
Linney et al. Nature 308:470–472 1984.*
Verma et al. Nature 389:239–242 1997.*

* cited by examiner

*Primary Examiner*—Robert A. Schwartzman
*Assistant Examiner*—Katharine F Davis
(74) *Attorney, Agent, or Firm*—TraskBritt PC

(57) ABSTRACT

Genetic modification of pluripotent hemopoietic stem cells of primates (P-PHSC) by transduction of P-PHSC with a recombinant adeno-associated virus (AAV). Tile genome of the recombinant AAV comprises a DNA sequence flanked by the inverted terminal repeats (ITR) of AAV. The DNA sequence will normally comprise regulatory sequences which are functional in hemopoietic cells and, controlled by these regulatory sequences, a sequence coding for a protein or RNA with a therapeutic property when introduced into hemopoietic cells. Preferred examples of DNA sequences are the human lysosomal glococerebrosidase gene, a globin gene from the human β-globin gene cluster, a DNA sequence encoding an RNA or protein with anti-viral activity, the α1-antitrypsin gene and the human multidrug resistance gene I (MDRI). The invention provides for effective gene therapy with PHSC of primates, in particular humans.

28 Claims, 7 Drawing Sheets

Figure 1:
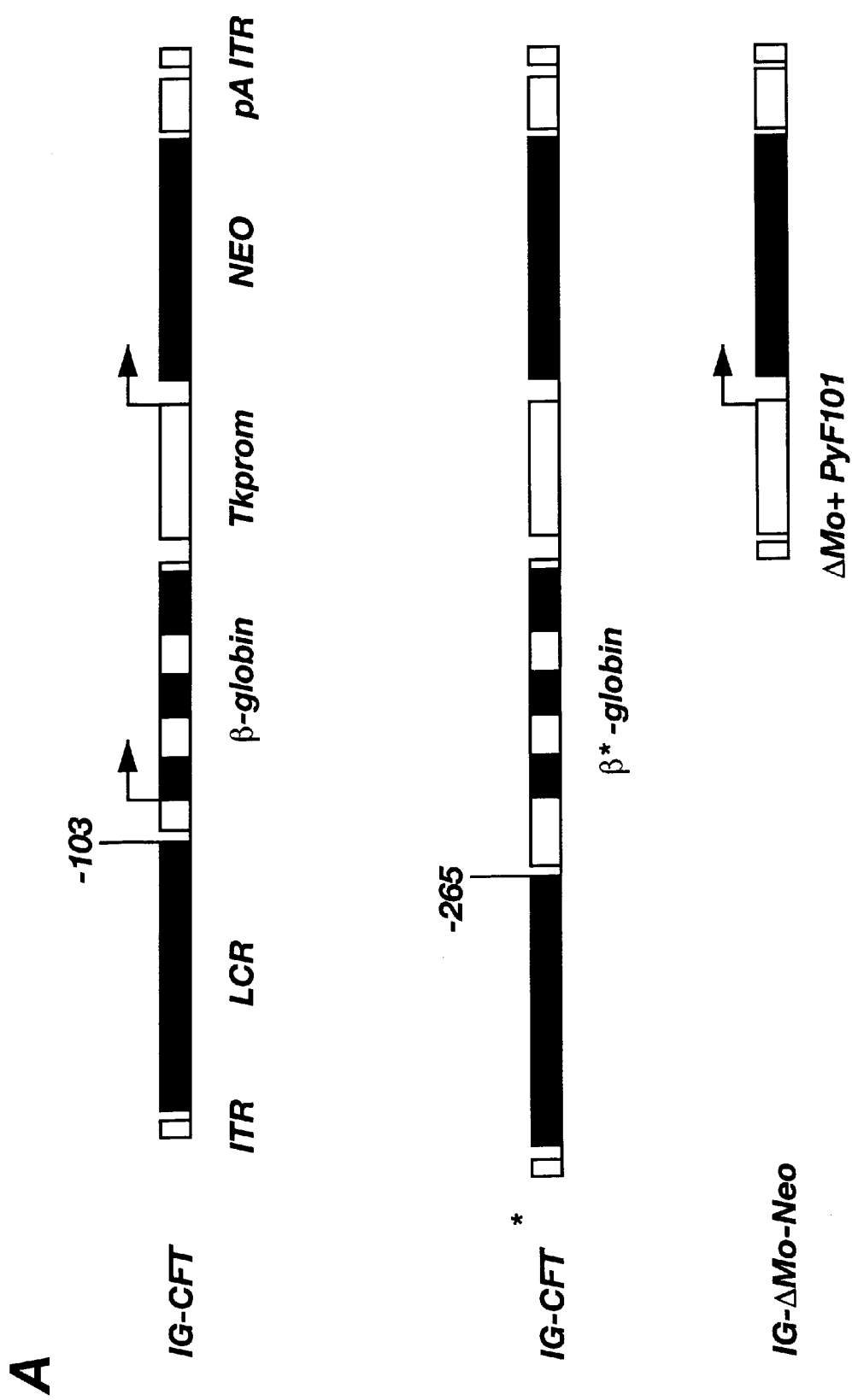

5' UTR β-globin:

5'-ACATTTGCTTCT- GACACAACTGTGTTCACTAGCAACCTCAAACAGACACC ATG (Seq. In No. 9)
5'-ACATTTGCTTCTAGACACAACTGTGTTCACTAGCAAgCTTAAACAGACACC ATG (Seq. In No. 10)
   --XbaI--                              --HindIII--                |Startcodon 5' UTR β*-globin:

Fig. 1B

| Week after Transplantation | rh 9128 WBC | rh 9128 Gran | rh 9170 WBC | rh 9170 Gran |
|---|---|---|---|---|
| -4 | -/- | - | - | - |
| -3 | | | | |
| -2 | | | | |
| -1 | | | | |
| 0 | | | | |
| 1 | - | - | +/- | + |
| 2 | | | | |
| 3 | | | | |
| 4 | - | - | - | - |
| 5 | -/+ | - | - | - |
| 6 | + | | + | + |
| 7 | | | - | - |
| 8 | - | - | | |
| 9 | ■ | ■ | | |
| 10 | + | + | | |
| 11 | -/- | - | ■ | ■ |
| 12 | + | | | |
| 13 | ■ | ■ | | |
| 14 | | | | |
| 15 | + | | | |
| 16 | ■ | ■ | | |
| 17 | | | | |
| 18 | - | | | |
| 19 | + | | | |
| 20 | | | | |
| 21 | | | | |
| 22 | - | | | |
| 23 | ■ | ■ | | |
| 24 | | | | |
| 25 | - | | | |
| 26 | - | | | |
| | ■ | ■ | | |

■ Taxotere Treatment

*Fig. 2*

SEQUENCE LISTING

<160> NUMBER OF SEQ ID NOS: 10

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence:neo specific primer

<400> SEQUENCE: 1
ggggtaccgc cgccgccacc atgattgaac aagatggatt gc      42

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence:neo specific primer

<400> SEQUENCE: 2
ttctccggcc gcttgggtgg      20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence:neo specific primer

<400> SEQUENCE: 3
ggcaggagca aggtgagatg      20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:neo specific primer

<400> SEQUENCE: 4
ccatgatgga tactttctcg      20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence:neo specific primer -continued

```
<400> SEQUENCE: 5
tagcgttggc tacccgtgat                                              20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence:neo specific
      primer

<400> SEQUENCE: 6
tgccgtcata gcgcgggtt                                               19

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:beta-globin
      specific primer

<400> SEQUENCE: 7
ggaattattc ggatctatcg at                                           22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence:beta-globin
      specific primer

<400> SEQUENCE: 8
tccttaaacc tgtcttgtaa cc                                           22

<210> SEQ ID NO 9
<211> LENGTH: 53
<212> TYPE: DNA
<213> ORGANISM: Homo sapiens

<400> SEQUENCE: 9
acatttgctt ctgacacaac tgtgttcact agcaacctca aacagacacc atg         53

<210> SEQ ID NO 10
<211> LENGTH: 55
<212> TYPE: DNA
<213> ORGANISM: Homo sapiens

<400> SEQUENCE: 10
acatttgctt ctagacacaa ctggtgttca ctagcaagct taaacagaca ccatg       55
```

GENETIC MODIFICATION OF PRIMATE HEMOPOIETIC REPOPULATING STEM CELLS

RELATED APPLICATIONS

This application claims priority under 35 U.S.C. §§ 119, 120 & 365 from, and is a continuation of, International Application No. PCT/NL97/00631, filed on Nov. 19, 1997, designating the United States of America. This application further claims benefit under 35 U.S.C. § 119 to EPO patent application 96203444.3 filed Dec. 5, 1996.

FIELD OF THE INVENTION

The present invention relates to the field of gene therapy and, more particularly, relates to DNA molecules derived from adeno-associated virus (AAV) for the genetic modification of primate hemopoietic stem cells.

BACKGROUND OF THE INVENTION

Genetic modification of pluripotent hemopoietic stem cells from primates (P-PHSC) has been an elusive goal for many years. Retrovirus vectors have been used in the past with limited success [1]. Though retroviral vector technology is still improving, progress in increasing the transduction of P-PHSC is slow. This is due to the fact that a solution is not straightforward and that the P-PHSC cannot be identified by a rapid in vitro culture method [1]. Though culture of hemopoie-tic progenitor cells is possible, the in vitro transduction levels of these cells do not reflect transduction of P-PHSC that in vivo can grow out to give long term reconstitution in multi-hemopoietic lineages [1,2,3]. Although long-term in vitro culture assays, such as, e.g., the so-called LTC-IC assay, have long been considered relevant assays for P-PHSC, it is now generally accepted that only a very minor sub-population of the cells identified in long-term in vitro culture assays are P-PHSC. Therefore, genetic modification of long-term in vitro cultured cells, even very efficient genetic modification, does not provide any relevant information on genetic modification of P-PHSC. Furthermore, although increasing knowledge is being gathered on the expression of cell surface markers on P-PHSC, P-PHSC can also not be identified by their phenotype. P-PHSC are known to express the CD34 molecule and to be negative for many other hemopoietic cell surface markers, but even the purest P-PHSC population that can currently be phenotypically characterized contains only few P-PHSC. Due to this, transduction has to be evaluated by laborious and lengthy in vivo studies using a bone marrow transplantation setting where the stem cells in the bone marrow were transduced ex vivo and subsequently transplanted back into monkey or human. Transduction of P-PUSC is verified by the long term persistence of genetically modified hemopoietic cells. Currently, the most efficient method for the transduction of P-PHSC is by means of retroviral vectors. Using such vectors, it is possible to transduce approx. up to 0.01–0.1% of the P-PHSC [3,4,5,6,7]. The limitation of retroviral transduction is most likely due to a restricted expression of the retrovirus receptor on P-PHSC, combined with the fact that P-PHSC are usually not in cell cycle, whereas retroviral vectors do not efficiently transduce non-dividing cells [8,9,10,11].

A number of methods have been devised to improve the P-PHSC transduction by retroviral vectors such as pseudotyping retroviruses using VSV (Vesicular Stomatitis Virus) envelope protein or GALV (Gibbon Ape Leukemia Virus) envelope proteins to target different and possibly more abundantly present receptors on the cell membrane. Other strategies were directed toward improving the number of cycling P-PHSC in the transplant. To date, this did not result in-a significant improvement of P-PHSC transduction.

In contrast to P-PHSC, murine PHSC are very easily transduced by the current generation of retroviral vectors. This observation, made in experiments using retroviral vectors, shows that successful gene transfer into murine PHSC is by no means indicative for successful gene transfer into P-PHSC. One can think of a number of different possible reasons for this observation. We hypothesized that it is theoretically not optimal to use a vector system that has evolved in murine animals for humans. Though the cellular processes involved in the murine retrovirus life cycle are conserved between murine mammals and primates, it is very well possible that the evolutionary divergence of the species resulted in structural differences in the related proteins that affect the functional efficiency of the murine virus proteins in human cells and, thus, affect the transduction process. To avoid these problems, we turned to a different vector system based on the human virus adeno-associated virus (AAV).

AAV is a human virus of the parvovirus family. The AAV genome is encapsidated as a linear single-stranded DNA molecule of approximately 5 kb. Both the plus and the minus strand are infectious and are packaged into virions [12,13]. Efficient AAV replication does not occur unless the cell is also infected by adenovirus or herpes virus. In the absence of helper virus, AAV establishes a latent infection in which its genome is integrated into the cellular chromosomal DNA. The AAV genome contains two large open reading frames. The left half of the genome encodes regulatory proteins, termed REP proteins, that govern replication of AAV-DNA during a lytic infection. The right half encodes the virus structural proteins VP1, VP2 and VP3 that together form the capsid of the virus. The protein coding region is flanked by inverted terminal repeats (ITRs) of 145 bp each, which appear to contain all the cis-acting sequences required for virus replication, encapsidation and integration into the host chromosome [14,15].

In an AAV-vector, the entire protein-coding domain (±4.3 kb) can be replaced by the gene(s) of interest, leaving only the flanking ITRs intact. such vectors are packaged into virions by supplying the AAV-proteins in trans. This can be achieved by a number of different methods, one of them encompassing a transfection into adenovirus infected cells of a vector plasmid carrying a sequence of interest flanked by two ITRs and a packaging plasmid carrying the in trans required AAV protein coding domains rep and cap [15,16,17,18,19]. Due to the stability of the AAV-virion, the adenovirus contamination can be cleared from the virus preparation by heat inactivation (1 hr, 56° C.). In initial studies, virus preparations were contaminated with wild-type AAV, presumably due to recombination events between the vector and the helper construct [16,17,18,19]. Currently, wild-type AAV-free recombinant AAV stocks can be generated by using packaging constructs that do not contain any sequence homology with the vector [15].

Several characteristics distinguish AAV-vectors from the classical retroviral vectors (see also table 1). AAV is a DNA virus which means that the gene of interest, within the size-constraints of AAV, can be inserted as a genomic clone [20, 21]. Some genes, most notably the human β-globin gene, require the presence of introns for efficient expression of the gene [22]. Genomic clones of genes cannot be incorporated easily in retroviral vectors, as these will splice out the introris during the RNA-stage of their life-cycle [23].

In human target cells, wild-type AAV integrates, preferentially, into a discrete region (19q13.3-qter) of chromosome 19 [24,25,26]. This activity might correlate with rep-gene expression in the target cell, since it was found that the large rep-proteins bind to, the human integration site in vitro [27]. AAV-vectors do integrate with high efficiency into the host chromosomal DNA, however, thus far, they do not share the integration site specificity of wtAAV [20]. Site-speciftc integration would be of great importance since it reduces the risks of transformation of the target cell through insertional mutagenesis. Wild-type AAV is, thus far, not associated with human disease. Evidence is accumulating that AAV infection of a cell, indeed, forms an extra barrier against its malignant transformation (reviewed in [28]). In contrast to retroviral vectors where, due to the extended packaging signal, parts of the gag-region need to be present in the vector, the entire protein coding domain of AAV can be deleted and replaced by the sequences of interest, thus totally avoiding any inTmunogenicity problem associated with viral protein expression in transduced target cells. One drawback of AAV-vectors is that they are derived from a human virus. Thus, patients treated with an AAV-vector might become exposed to wtAAV which, in the presence of a helper virus such as adeno-virus or herpes simplex virus, can supply the virus replication and packaging proteins in trans and thus induce spread of the recombinant AAV-virus into the environment. This is a feature not shared by the currently used MuLV-derived retroviral vectors; wild-type MuLV's do not normally cause infections in humans. The risk of recombinant AAV spread into the environment must, however, not be overestimated since it requires the presence of wtAAV and a helper virus. This is not a frequently occurring situation. In addition, during the integration process of AAV-vectors, often the ITRs undergo some form of recombination leading to loss of function [15]. Such proviruses cannot be rescued and, thus, provide an additional safety level of these vectors.

The first AAV-vectors were made by replacing part of the AAV-coding region with either the Chloramphenicol Acetyltransferase (CAT) or the neon gene [16,17]. All of these vectors retained either a functional rep- or a functional cap-coding region. Recombinant virus was generated by cotransfection with a plasmid containing a complete AAV-genome. The recombinant AAV-CAT virus conferred Chloramphenicol Acetyltransferase activity to 293 cells [16] whereas the recombinant $neo^R$ virus conferred G418-resistance to Human Detroit 6 cells, KB-cells and mouse L-cells [71].

Currently, AAV-vectors are made that are totally devoid of AAV-protein coding sequences. Typically, virus is made from these vectors by complementation with a plasmid carrying the AAV-protein coding region but no ITR-sequences [15].

AAV-vector technology is under development for a number of different therapeutic purposes and target tissues. The as yet most developed system is, perhaps, AAV-vector mediated gene transfer to lung cells [29,30]. AAV-vectors carrying the $neo^R$ gene or the CAT gene were transferred and expressed efficiently in airway epithelial cells [29]. An AAV-vector carrying sequences 486–4629 of the human Cystic Fibrosis Transmembrane conductance Regulator (CFTR) gene fused to a synthetic oligonucleotide supplying the translation start site, was capable of complementing Cystic fibrosis (CF) in vitro [31]. In addition, stable gene transfer and expression was reported following infection of primary CF nasal polyp cells and after in vivo delivery of the AAV-CVTR vector to one lobe of the rabbit lung [30]. In vivo, the vector DNA could be detected in 50% of the nuclei at 3 months post-administration. Although the prevalence of the vector decreased after this time point, still ±5% of the nuclei were positive at the six months time point [30]. The presence of the vector correlated well with expression of RNA and recombinant protein which where still detectable at the six months follow up [30].

AAV-vector mediated gene transfer into murine hemopoietic cells was demonstrated by the conference of G418 resistance to murine in vitro colony forming units (CFU) following infection with a recombinant AAV-vector carrying the $neo^R$-gene [32,33]. The presence of the vector in the progeny of CFU-GM (colony forming units-Granulocyte Macrophage) and BFU-E (burst forming units-Erythrocyte) was verified by means of PCR (Polymerase Chain Reaction). The efficiency of gene transfer varied between 0.5% and 15% [33]. Efficient gene delivery (up to 80%) into human hemopoietic progenitors and human $CD34^+$ cells with AAV-$neo^R$ vectors has also been reported [34,35,36, 37]. These studies demonstrated that rAAV vectors were able to deliver their DNA to the nucleus of the hemopoietic progenitor cells that can be cultured in vitro. Though delivery of the vector DNA to the nucleus of cells demonstrates the presence of a functional virus receptor on the surface of the target cells, delivery of rAAV to the nucleus of cells is not directly related to the integration of that DNA into the host cell genome (discussed later and presented in table 2). Recombinant adeno-associated virus DNA present as an episome in the cells is known to refrain from integration into the host cell genome in non-dividing tissue culture cells [38]. Integration of rAAV in $CD34^+$ cells and in vitro growing colonies (CFU-C) was demonstrated in 1996 by Fischer-Adams et al. [59]. Stable transduction of P-PHSC is neither taught nor suggested in any of these prior art documents, however. None of the above mentioned studies discloses delivery and integration of rAAV to P-PHSC, the only relevant hemopoietic cell type for long term persistence of transduced cells in vivo.

We are developing rAAV gene transfer into P-PHSC for the treatment of β-thalassemia and Sickle cell anemia. Both diseases severely affect the function of erythrocytes in these patients. β-thalassemic erythrocytes contain insufficient β-globin chains, whereas mutant β-globin chains are made in sickle cell anemia (for review see [39]). Both diseases severely affect erythrocyte function which can be alleviated by persistent γ-globin gene expression in the adult patient in which case fetal hemoglobin is formed [40]. Both inherited diseases are recessive in nature which indicates that one functional intact copy of the adult β-globin gene is sufficient to ameliorate the phenotype.

Globin abnormalities were discarded as targets for gene therapy attempts in the early days of gene therapy research. This was largely due to the extremely complicated expression patterns of globin-like genes [41]. Globin-synthesis is highly regulated during development and confined to cells of the erythroid lineage. Furthermore, the expression of α- and β-globin like chains is regulated such that they are maintained at a 1 to 1 ratio in the cell. Such careful control of gene expression is not easily obtained. Expression vectors carrying the human β-globin gene with its promoter and local enhancer elements can direct erythroid specific globin RNA expression [42]. However, typically, the levels are less than 1% of the endogenous globin RNA.

Recently, sequences 50–60 kb upstream of the β-globin gene were discovered that direct the high level, tissue specific, copy number dependent and position independent expression of the β-globin gene [43]. This region, designated the Locus Control Region (LCR), is characterized by four strong erythroid-specific DNaseI hypersensitive sites (HS1–4) [44]. Fine-mapping of the active sequences in the LCR identified four fragments of ±400 bp in length that each coincide with one HS site. Walsh et al incorporated a marked γ-globin gene and the core fragment of HS2 together with the neo$^R$ gene into an AAV-vector [20]. Infected and G418 selected pools and clones of K562 cells produced the marked γ-globin RNA to 50–85% compared to the normal level expressed by one endogenous γ-globin gene [20,45]. A drawback of this vector is that the γ-globin gene and promoter used in these studies are specific for expression in fetal erythroid tissue and, thus, not ideal for use as a therapeutic agent in adult humans, tInorporation of β-LCR sites 1, 2, 3 and 4 in a vector containing the adult specific human β-globin gene resulted in a very high regulated expression in MEL (murine erythroleukemia) cells, the best in vitro marker cell line for regulated erythroid expression in adult tissue [46]. The present invention describes the use of this and similar vectors in the transduction of P-PHSC.

The term "infectious particles" is used herein to refer to AAV particles that can deliver their packaged DNA to the nucleus of cells and replicate in the presence of adenovirus and wtAAV.

The term "transducing particles" is used herein to refer to AAV particles that can deliver their packaged DNA to the nucleus of target cells where the packaged DNA is released and integrates into the chromosomal DNA of the target cells.

SUMMARY OF THE INVENTION

This invention provides a process of genetic modification of pluripotent hemopoietic stem cells of primates (P-PHSC), comprising introducing a nucleic acid molecule based on adeno-associated virus (AAV), in particular a recombinant AAV, which is derived from human AAV, into P-PHSC, preferably by transduction. The genome of the recombinant AAV comprises a DNA sequence flanked by the inverted terminal repeats (ITR) of AAV, or functional analogs or fragment thereof. Normally and preferably, but not necessarily, said DNA sequence will be a non-AAV DNA sequence, in particular a therapeutic DNA sequence, According to a preferred embodiment of the invention, the DNA sequence comprises regulatory sequences functional in hemopoietic cells (in particular hemopoietic stem cells) and, under the control of said regulatory sequences, a sequence coding for a protein or RNA with a therapeutic property when introduced into hemopoietic (stem) cells. Preferred examples of the DNA sequence comprise the coding sequence of such genee as the human lysosomal glucocerebrosidase gene (E.C.3.2.1.45), a globin gene from the human β-globin gene cluster, a DNA sequence encoding an RNA or protein with anti-viral activity, the α1-antitrypsin gene and the human multidrug resistance gene I (MDRI).

In a particularly preferred embodiment, the DNA sequence comprises the human β-globin gene inclusive of at least one of its introns or functional analogs thereof, under transcriptional control of a functional part of the β-globin promoter or functional analogs thereof, and being operably linked to erythroid-specific DNaseI hypersensitive sites from its Locus Control Region (LCR), more particularly, the β-LCR elements HS4, HS3 and HS2 or functional analogs thereof.

The DNA sequence may also comprise a selectable marker gene useful in hemopoietic stem cells, such as a neo$^R$ gene, under transcriptional control of a herpes simplex virus (HSV) thymidine kinase (tk) promoter or functional analogs thereof or a ΔMo+PyF101 Long Terminal Repeat (LTR) promoter.

The P-PHSC may be obtained from primate bone marrow, cord blood or peripheral blood and, preferably, from a human. The P-PHSC may be exposed in vitro to proliferation stimulating compounds, such as interleukin 3 or a functional analog or fragment thereof.

DETAILED DESCRIPTION OF THE INVENTION

The present invention is based on the discovery that adeno-associated virus-derived vectors efficiently transduce primate pluripotent hemopoietic stem cells. Adeno-associated virus has not been reported to transduce pluripotent hemopoietic stem cells of primates and AAV-derived vectors have not been shown to transduce hemopoietic cells with in vivo repopulating ability, In addition, it is surprising that the vector integrates with high efficiency into P-PHSC, even though most of the P-PHSC are not actively dividing at the time of infection. This is surprising, since it has been established that rAAV integration in dividing cells occurs 200 times more efficiently in dividing, as opposed to non-dividing cells [38]. Also, it was reported that primary cells are much less efficiently transduced by rAAV than immortalized cell lines [47]. In addition, it was reported that orf 6 from adenovirus E4-region stimulates transduction by recombinant AAV [48]. In a gene therapy setting, it is undesirable to have functionally active adenovirus present due to toxicity problems caused by the virus directly or the immune system of the patient. At the Keystone Symposium on Molecular and Cellular Siology, Taos, N. Mex. Feb. 4–10, 1996, Prof. A. Nienhuis presented a paper stating that they transduced rhesus monkey CD34$^+$ cells and, subsequently, autologously transplanted the infected cells [49]. Analysis of the peripheral blood cells circulating in blood with a polymerase chain reaction specific for the rAAV revealed that cells carrying the rAAV were only detected up until 7 days post transplantation [49], i.e. P-PHSC were not transduced by rAAV in their experiment. Nonetheless, the present invention demonstrates that an adeno-associated virus-derived vector may be used to deliver exogenous DNA efficiently to cells of the hemopoietic system with long term repopulating ability.

The current perception of AAV-integration into the cellular host chromosome is that the pre-integration complex is stable in cells. Although integration occurs more efficiently in dividing cells, the pre-integration complex is stable in non-dividing cells and integrates when the cell is triggered to undergo cell cycling [38,60]. The primate-derived hemopoietic stem cells and committed progenitor cells upon autologous transplantation into an irradiated recipient are triggered into cycle to repopulate the destroyed hemopoietic system. For this reason, it is generally believed that the hemopoietic cells need not be triggered in vitro. For this reason, protocols to transduce hemopoietic progenitor cells with rAAV do not involve culturing the cells in the presence of hemopoietic growth factors. Although this reasoning is very plausible with the current information, we devised experiments to investigate the effect of in vitro culture of hemopoietic stem cells and the in vitro stimulation with hemopoietic growth factors.

As used herein, the term "recombinant AAV vector" means a DNA sequence flanked at each end by an AAV-ITR or functional equivalent or part thereof. The recombinant AAV vector can be used directly or be packaged into a complex before use, As used herein, the term "complex" is defined as a combination of two or more components physically linked to each other through hydrophobic, hydrophilic or electrostatic interactions or covalent bonds, whereby one component of the complex at least is a recombinant AAV molecule. Other components of the complex can comprise, but are not limited to, one or a combination of liposomes, calcium phosphate precipitate, polylysine, Adenovirus, Adenovirus proteins, Rep78, Rep68, AAV capsids or the AAV capsid proteins VP1, VP2 or VP3. In a preferred embodiment the complex consists of the recombinant AAV vector and the AAV capsid proteins. This complex can be, but is not limited to, the form of an intact virion or particle where the recombinant AAV vector is packaged inside an AAV capsid or functional analogs thereof.

As used herein, the term "functional analogs" refers to the same activity in kind, but not in amount or degree, i.e. not quantitatively.

When the recombinant AAV is packaged into AAV particles, the size of the DNA sequence will be limited by the size constraints for packaging into AAV particles which, with the current state of the technology, is about 5 kb. The DNA fragment preferably does not contain sequences functionally analogous to the terminal resolution site in the AAV-ITR as this might interfere with the stability of the recombinant vector. The DNA sequence can be any sequence with therapeutic properties when introduced into hemopoietic stem cells, but the DNA sequence preferably encodes one or more proteins or RNA with therapeutic properties when expressed in hemopoietic cells. Non-limiting examples of such sequences are the human β-globin gene operably linked to cis-acting sequences for erythroid specific physiological expression, the human lysosomal glucocerebrosidase gene (E.C3.2.1.45), the α1-antitrypsin gene, a DNA sequence encoding an RNA or protein with anti-viral activity or the multidrug resistance gene I (MDRI). AAV-ITR sequences may be obtained from AAV serotypes 1, 2, 3, 4 or 5. Alternatively, mutant or recombinant ITR sequences can be used, which retain the essential properties of the AAV-ITR prototype, examples of which are described in Lefebvre et al, [50].

Packaging of rAAV into AAV-virions can be achieved using a variety of different methods. All methods are based on bringing the necessary proteins and rAAV-containing DNA in an environment that supports the replication and packaging of rAAV, One method relies on the transfection of adenovirus 5 infected human cells with a plasmid carrying the rAAV-DNA together with a plasmid containing expression cassettes for the AAV-genes rep and cap. Upon continued culture of the manipulated cells, rAAV is replicated and packaged. After three days, the cells are harvested and the accumulated recombinant virions are released from the cells [15–19]. A variation on the packaging system described above is the use of packaging cells that carry all or part of the relevant sequences stably integrated in their genome (i.e. the recombinant AAV vector, the rep-gene, the cap-gene, and the relevant protein coding domains of the helper virus). When only partial packaging cells are used, the missing packaging functions have to be supplied externally via transtections of plasmids carrying the functions or virus infection. The helper virus functions are required for efficient packaging of recombinant AAV. For most applications, the helper virus is inactivated or separated physically from the recombinant AAV virions before using the recombinant AAV virions for the transduction of cells [15–19]. Recombinant AAV vectors can be packaged by adding the recombinant AAV-DNA to protein extracts or mixtures of protein extracts of cells that expressed all or part of the relevant proteins for the replication and packaging of recombinant AAV. When protein extracts are used from cells expressing only some of the relevant proteins for packaging of recombinant AAV, the missing proteins can be supplied externally in purified form.

The rep-gene can be derived from AAV serotypes 1–5 or functional analogues thereof either obtained through non-essential mutations in the rep-genes or through the isolation of genes with similar capabilities such as the Human Herpesvirus 6 AAV-2 rep gene homologue [58].

The cap-gene can be derived from AAV serotypes 1–5 or functional analogues thereof obtained through non-essential mutations in the cap-genes. Alternatively, the cap-gene sequences can be altered through the replacement or addition of sequences rendering the produced virion new or altered target cell specificities.

Recombinant AAV virions produced by the methods described above can be purified and concentrated using biological, physical or chemical separation techniques such as, but not limited to, antibody affinity purification, density gradient centrifugation or ion exchange chromatography. Alternatively, the virions produced can be used in an unpurified form.

As used herein, pluripotent hemopoietic stem cells from primates (P-PHSC) are functionally defined as cells from primates with the capability to form and maintain an entire hemopoietic system, ranging from mature T-cells, B-cells, macrophages or erythrocytes to new P-PHSC. P-PHSC display this capability in unmanipulated primates or upon their autologous transplantation. Sources of P-PHSC are the bone marrow, the peripheral blood or cord blood. P-PHSC can be collected from unmanipulated primates or from primates treated with compounds such as, but not limited to, cytostatic drugs or hemopoiatic growth factors to activate, recruit or otherwise potentiate the P-PHSC.

Transduction of P-PHSC is preferably performed ex vivo, following harvesting of the P-PHSC from a suitable source, and after the transduction the transduced cells are autologously transplanted. In a preferred embodiment of the invention, the P-PHSC are cultured during their ex vivo transduction, where it is most preferred that during this culture the P-PHSC are stimulated with at least one hemopoietic growth factor, such as, e.g., interleukin-3. Alternatively, P-PHSC transduction is performed in vivo when suitable methods have been developed to target the recombinant AAV vector in vivo to P-PHSC.

BRIEF DESCRIPTION OF THE TABLES AND DRAWINGS

Table 1 Key properties of Adeno-associated virus vectors and amphotropic retrovirus vectors.

Table 2 Characterization of recombinant AAV preparations useful for the transduction of primate PHSC.

Table 3 Transduction of primate PHSC: culture and infection conditions.

IP=Infectious Particles (titrated in RCA);

TP=Transducing Particles (titrated on MEL cells).

Table 4 Transduction of primate PHSC: Hemopoietic data.

FIG. 1A Recombinant AAV-vectors useful for the transduction of primate PHSC.

ITR=Adeno-associated virus inverted terminal repeat,

LCR=Core sequences from hypersensitive sites 4, 3 and 2 from the β-globin locus control region.

−103=human β-globin gene promoter fragment extending −103 upstream of the transcription start site.

−265=human β-globin gene promoter fragment extending −265 upstream of the transcription start site.

β-globin=human β-globin gene with modified intron 2 (see text and 21).

Tkprom=Herpes Simplex Virus Thymidine kinase gene promoter (approx. 500 bp NarI-BglII fragment)

NEO=BglII-SmaI fragment from *E. coli* Tn5 transposon.

pA=Polyadenylation signal from Herpes Simplex Virus Thymidine Kinase gene λ.approx. 500 bp SmaI-NarI fragment).

β*-globin=human β-globin gene with in the 5' untranslated region three point mutations that generate two restriction enzyme sites (see FIG. 1B).

ΔMo+PyF101 a Moloney murine leukemia virus long terminal repeat fragment in which the Moloney enhancer is replaced by an enhancer from a mutant polyoma virus that was selected to grow on embryonal carcinoma cells [2,51, 52,53].

FIG. 1B Nucleotide sequence of the 5' untranslated region (UTR) of the normal (β) and the marked (β*) human β-globin gene.

FIG. 2 Detection of recombinant AAV in rhesus monkey peripheral blood cells. Blood cells were collected as described in the text. Peripheral blood mononuclear cells (WBC) were separated from the granulocytes (Gran) and a neospecific nested PCR was performed on the DNA of both cell types. DNA from the nested PCR was analyzed on agarose gels and compared to positive and negative control samples. The sensitivity of the nested PCR was such that approximately one rAAV-vector could be detected in a background of $10^5$ negative cells. (+) indicates the presence of a neo-specific band and (−) the absence of a neo-specific band in the agarose gel.

Figure 3A:
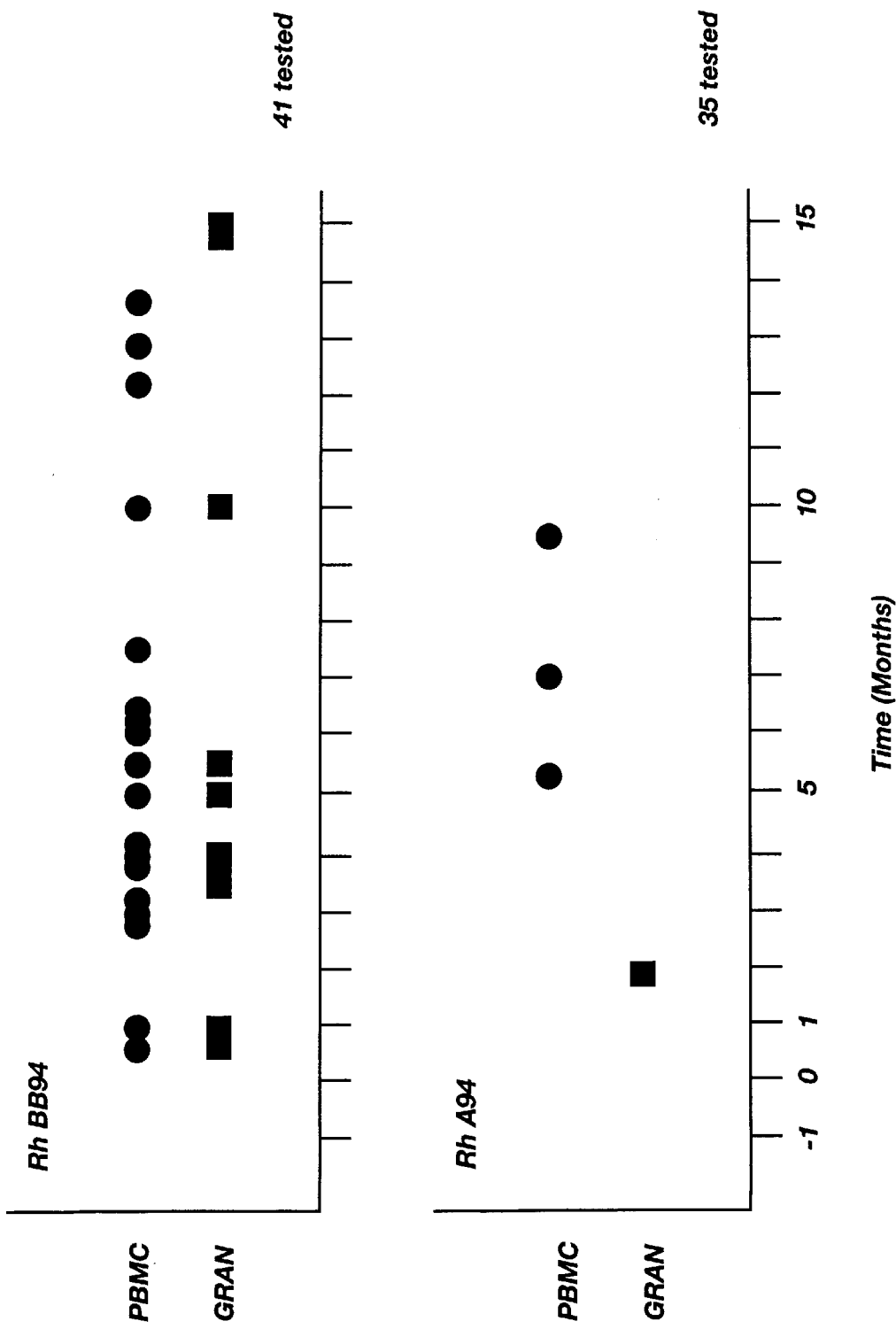
Figure 3B:
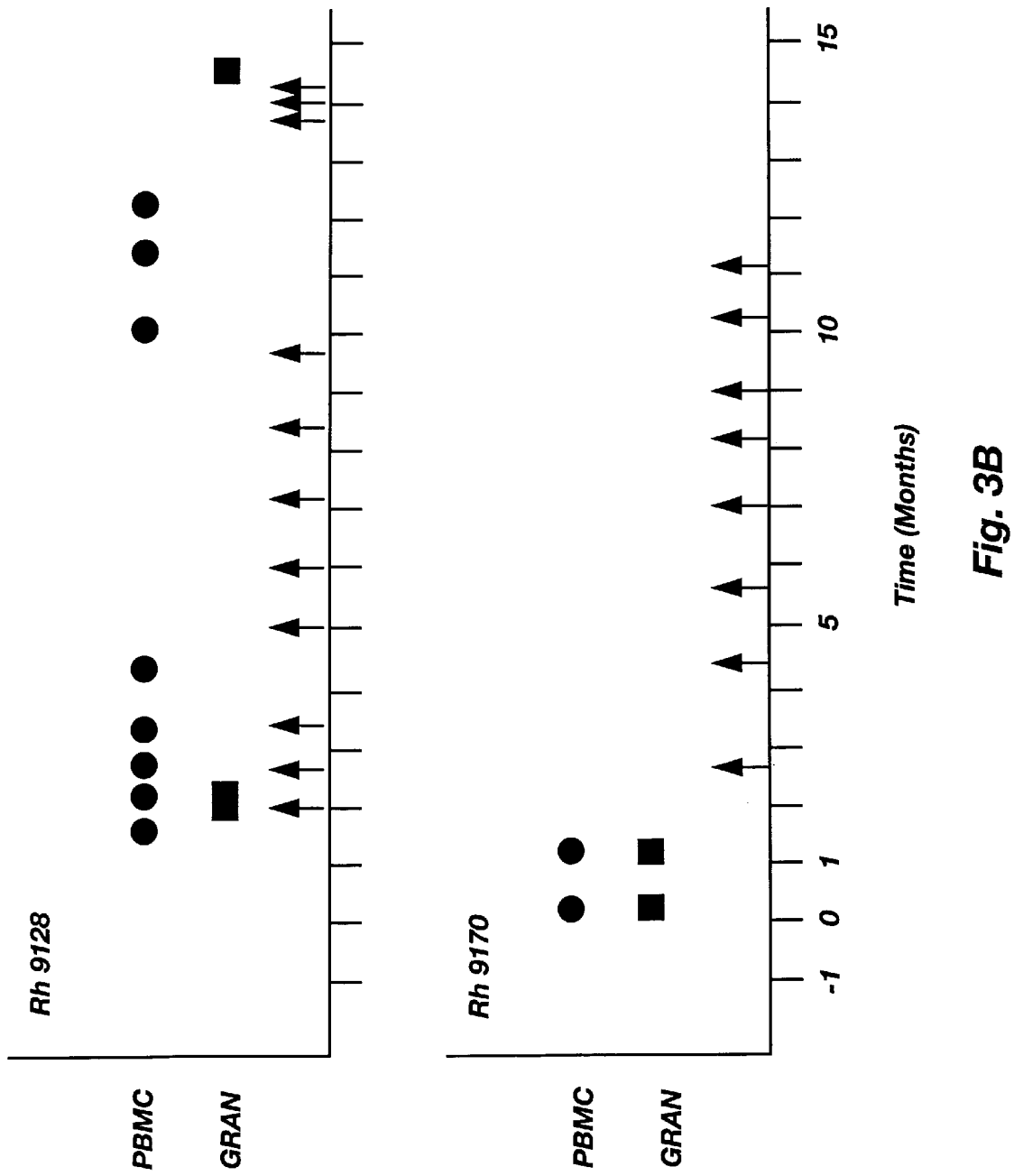

FIGS. 3A–3B Graphic representation of direct and nested neo-specitic PCR data from monkeys BB94 and A94 (FIG. 3a) and monkeys 9128 en 9170 (FIG. 3b). The data on the latter two monkeys shown in FIG. 2 are included in FIG. 3 as well. For clarity, negative PCR-results were not included in the graphs. Closed circles (PBMC) and closed squares (Granulocytes) indicate the time-points after transplantation at which the vector was detected. Arrows in FIG. 3b indicate the time-points at which docetaxel (Taxotere) was administered.

Figure 4:
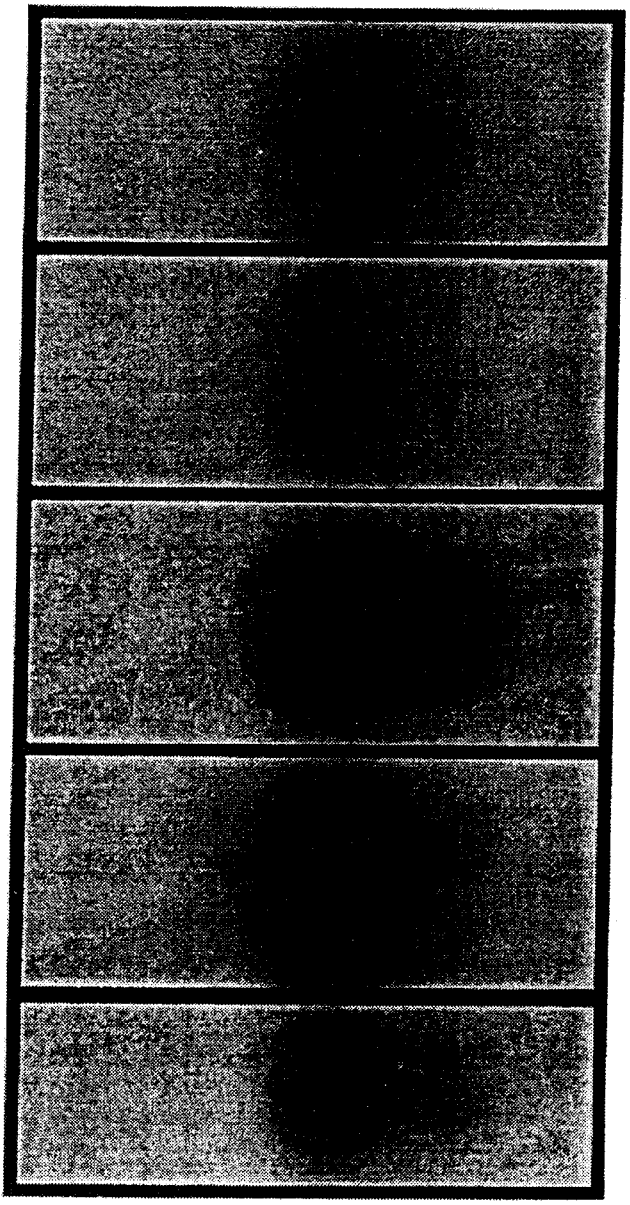

FIG. 4 Detection of neo-specific sequences in hemopoietic cells from rh BB94 at 16 months post transplantation. BM (bone marrow), PBMC (peripheral blood mononuclear cells), Gran (granulocytes).

Figure 5:
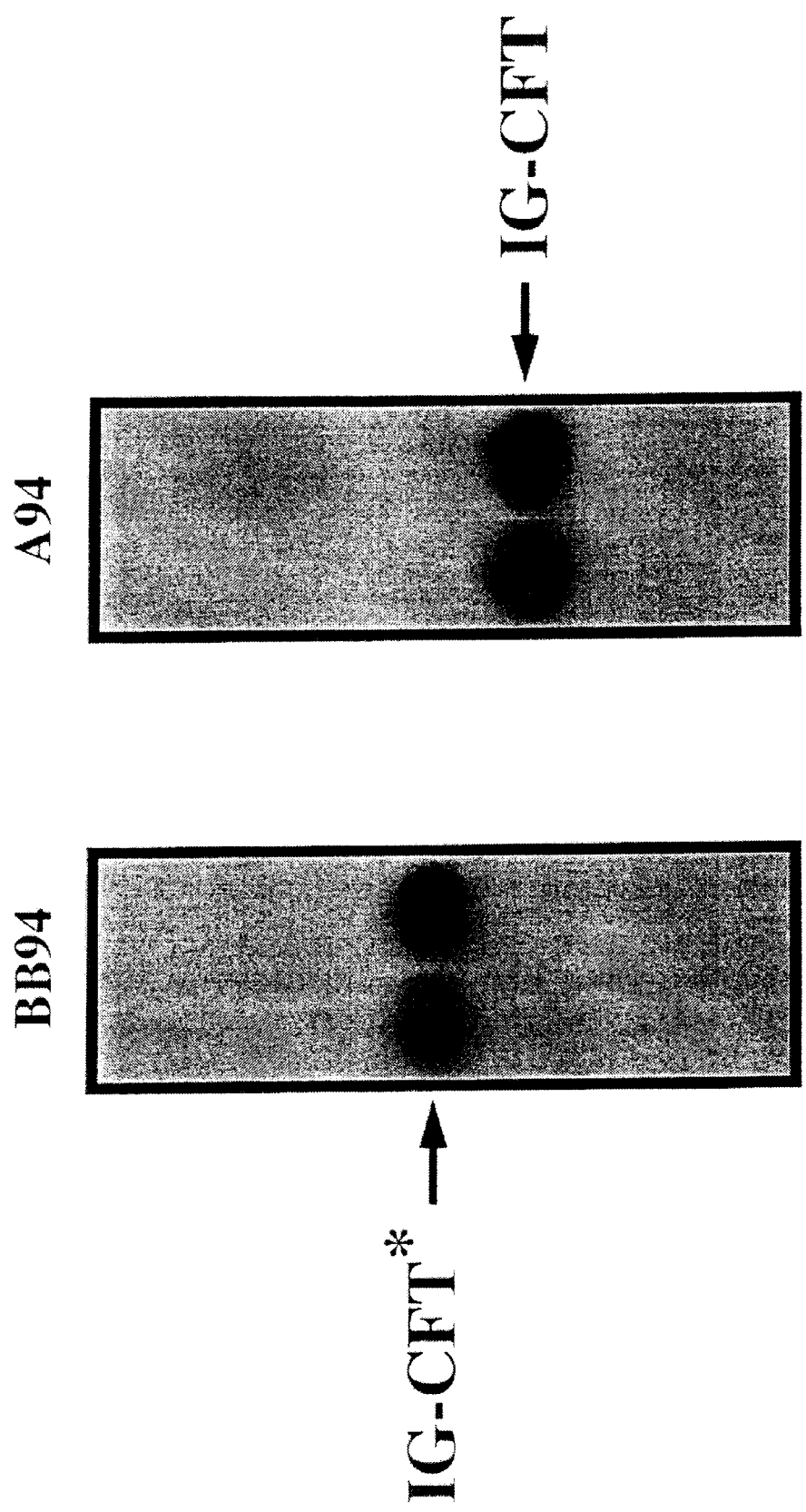

FIG. 5 Detection of vector specific globin sequences in rhesus monkey peripheral blood cells (samples from 2 months (A94) and 6 months (BB94) post-transplantation) With this PCR, the two vectors IG-CFT and IG-CFT* are discriminated since the size of the IG-CFT* fragment is approximately 150 pb. longer than the fragment specific for IG-CFT.

EXAMPLE 1

Ligation of Recombinant AAV Vectors Containing the Human β-globin Gene and/or the $Neo^R$ Gene In order to determine whether recombinant AAV could transduce P-PHSC, it was necessary to generate appropriate vectors. We generated three different recombinant AAV-vectors, which are schematically represented in FIG. 1A. The ligation of the vector IG-CFT containing a human β-globin gene together with sequences from the β-globin locus control region and the $neo^R$-gene is described in [21], IG-CFT* differs from IG-CFT in the size of the human β-globin promoter and in the presence of three point mutations in the 5' untranslated region (UTR) of the human β-globin gene, In IG-CFT*, the promoter driving β-globin expression extends 265 bp upstream of the transcription start site instead of the 103 bp in IG-CFT. In IG-CFT*, three point mutations in the 5' UTR of the human β-globin gene created two new restriction sites, one for XbaI and one for HindIII, see also FIG. 1B.

IG-ΔMoNeo (depicted in FIG. 1A) contains the rAAV-backbone (XbaI-fragment) from pSub201 [51], the NheI-SmaI promoter-fragment from the ΔMo+PyF101 LTR [53], the BglII-SmaI fragment from the Tn5-derived $neo^R$-gene followed by the SmaI-NarI poly-adenylation signal from Herpes Simplex Virus (HSV) Thymidine Kinase (TK) gene [54]. The elements were linked together using the polylinker from pbluescript $SK^+$ (Stratagene).

EXAMPLE 2

Production of Recombinant AAV from IG-CFT, IG-CFT* and IG-ΔMoNeo

The 293 cell line [55], which is a human embryonic kidney cell line transformed with Ads DNA, the A549 cell line, which is a human bronchial carcinoma cell line, and the C88 cell line [56], which is a murine erythroleukemia (MEL) cell line, were maintained in DMEM (GIBCO-BRL) containing 10% Fetal Calf Serum (FCS), 100 μg/ml streptomycin and 100 U/ml penicillin. Recombinant AAV was produced by transfecting a rAAV packaging plasmid and a vector plasmid into approx. 90% confluent permissive 293 cells. The cells were made permissive for AAV-replication by transfecting them with a plasmid capable of expressing all the relevant early genes from adenovirus but not the late genes or by infecting them with adenovirus ts149 with a multiplicity of infection of 20. The packaging plasmid was either pAAV/Ad [15] or pIM45, which contains sequences 146 to 4493 from wtAAV2 in the polylinker of pBluescript, The ratio of vector plasmid DNA to packaging plasmid DNA was 1:10 to accommodate the fact that the recombinant AAV vector upon expression from the packaging plasmid replicates, whereas the packaging plasmid does not replicate. For crude virus stocks, the cells were harvested in their own culture medium after two to three days and subjected to three freeze/thaw cycles. The latter was performed by intermittent freezing and thawing in liquid nitrogen and a 37° C. water bath. Cell debri was subsequently pelleted. (10 min, 200 g) and the supernatant was incubated at 56° C. for 1 hour to inactivate residual adenovirus. Concentrated high titer recombinant AAV stocks were prepared by harvesting the cells in there own culture medium, and washing in PBS (max. $10^7$ cells/ml). The virus was released from the cells by 3 freeze/thaw cycles and/or 30 sonication pulses of 1 second on ice to prevent warming. Cell debri was spun down and the supernatant was made a density of 1.4 by adding solid CsCl. After o/n centrifugation (50.000 r.p.m., 20° C., using a vti TI65.1 rotor in a Beckman ultracentrifuge), fractions were collected and rAAV was determined. Fractions containing rAAV were pooled and further concentrated in a centricon concentrator (Amicon) according to manufacturer's specifications. After concentration, the medium containing the virus was changed by two successive washes in the centricon concentrator, using Optimem culture medium (GIBCO-BRL).

EXAMPLE 3

Characterization of rAAV Preparations

To determine the effect of the different methods of virus preparation and the different processing steps on the quality of the various rAAV-batches, we characterized them for 5 parameters: 1) the capacity to deliver the desired DNA to the nucleus of the target cell by means of a replication center assay (RCA) described below, 2) the capacity to stably transduce cells and express the neo$^R$-gene by means of a limiting dilution on MEL cells followed by G418 selection, 3) the wild-type AAV titer in the batches by a RCA without added wtAAV, 4) the amount of replication proficient adenovirus in each preparation, and 5) the concentration of CsCl in the rAAV preparations that were purified using CsCl radients (See Table 2).

Replication Center Assay

The replication center assay (RCA) takes advantage of the fact that in a lytic infection of AAV up to $10^6$ AAV, genomes are produced inside a cell. This amount of DNA is sufficient for the radioactive detection of infected cells. To accomplish this, 293 cells were seeded in a flat bottom 96 wells plate such that they reached near confluence the following day. For a titration of recombinant AAV, the cells were infected with dilutions of recombinant virus stock, adenovirus ts149 (M.O.I. 20) and wtAAV-2 (M.O.I. 2). For a titration of the wild type AAV, the cells were infected with dilutions of recombinant virus stock and adenovirus ts149 (M.O.I. 20). The cells were subsequently incubated at 39° C. The next day, after 24 hours, the medium was replaced by ice-cold PBS containing 5 mM EDTA. After 5 to 20 min. on ice, a single cell suspension was made by rigorous pipetting. The cells were diluted in 5 ml PBS and sucked onto hybond N$^+$ filter circles (pore size 0.22 $\mu$M) of 3.6 cm diameter. Filters were incubated for 5 min in denaturation solution (0.4 M NaOH; 0.6 M NaCl) and 5 min in renaturation buffer (1,5 M NaCl; 1 M Tris-HCl, pH 7). Filters were washed and stored in 5xSSPE until hybridization. Filters were hybridized with a recombinant AAV specific probe for the determination of the recombinant AAV titer and hybridized with a wild type AAV specific probe for the determination of the wild-type AAV titer.

MEL-cell transduction $1.5 \times 10^5$ MEL cells were seeded in 2 ml culture medium per well (24 wells plate, Falcon) and the appropriate dilution of rAAV virus was added. The cells were collected the next day and reseeded in 30 ml culture medium in a 75 cm$^2$ flask (Falcon). After three days, the medium was replaced by selection medium by spinning down the cells (200 g, rt) and resuspending the cells in fresh medium containing 1 mg/ml (dry weight) G418 (Gibco). Medium was replaced every three to four days. After fourteen days, the cultures were scored. When the cells had grown to confluency, the cultures were scored positive since the specific virus dilution contained rAAV capable of stably transducing MEL cells. Specific virus dilutions were scored negative when, after fourteen days, confluency had not been reached.

Adenovirus was determined by serial dilutions of the AAV virus stock on A549 (human bronchial carcinoma) cells. Dilutions were scored positive when cytopathic effect was visible after 6 days. Wild-type Adenovirus 5 stocks with a known titer were used as positive controls. CsCl concentrations in the AAV preparations were determined by flame photometry.

A summary of the characterization is given in Table 2. The infectious particle (IP) concentration, i,e. the capacity-to deliver rAAV-DNA to the nucleus of target cells determined in the PCA varied considerably among the different batches. Also the transducing particle (TP) concentration and the amount of wild-type AAV contamination varied considerably. Three batches had a IP to TP ratio of $10^4$, the 248 crude batch had a much lower ratio of 200.

EXAMPLE 4

Transduction and Autologous Transplantation of Rhesus Monkey Bone Marrow

Animal Care and Transplantation

The animals used for transplantation were 3–5 kg rhesus monkeys (Macaca mulatta), bred at the Biomedical Primate Research Centre (BPRC), Rijswijk, The Netherlands. Three weeks before transplantation, the animals were transferred to a laminar flow unit and selectively decontaminated in the digestive tract by treatment with metronidazole (40 mg/kg/day), during 5 days, followed by daily oral administration of ciprofloxacin (6.5 mg/kg/day), polymixin B (10 mg/kg/day) and nystatin (40 kU/monkey/day). A94 and BB94 received one administration of ivermectine 200 $\mu$g/kg anti-worm treatment approximately two weeks prior to transplantation. The monkeys were kept under barrier nursing and antimicrobial treatment until leukocyte counts exceeded a value of $1 \times 10^9$/liter. The day before transplantation, the monkeys received 5 Gy total-body X-ray irradiation. For this purpose, the animals were placed in a cylindrical polycarbonate cage which rotated 6 rpm around its vertical axis during irradiation from two opposing beams (physical parameters: 300 kV, 7 mA, 0.26 Gy/min dose rate, 0.80 m average focus-to-skin distance). Bone-marrow grafts were infused into a peripheral vein in a volume of 7.5 ml 0.9% NaCl. Supportive care after transplantation included blood transfusions of 15 Gray-irradiated thrombocytes when thrombocyte counts were below $40 \times 10^9$/liter, subcutaneous fluid upon indicationl,and red blood cell transfusions when hematocrit levels dropped below 0.2 l/l. Monkey 9128 was administered daily Baytrill s.c. for 2 weeks, 9 months after transplantation, as treatment of a Salmionella infection. Monkeys BB94 and A94 were treated for Streptococci septis and received cefamandolnafaat 50 mg/kg/day and tobramycine 3 mg/kg/day. A94 was additionally treated for Streptococci sepsis with amoxiline 9 mg/kg/day, clavulanic acid 2.5 mg/kg/day and ceftriaxone 50 mg/kg/day and with Amphotericin B 8 mg/kg/day for a yeast infection. Selective decontamination was stopped a few days after hemopoietic repopulation of the monkeys. Sepsis treatment was stopped 4 days after the body temperature had returned to normal and serum cultures were found to be sterile. Docetaxel (Taxotere®) treatment was given to monkeys rh9128 and rh9170 at indicated times (FIG. 3) at a dose of 50 mg/m$^2$. In monkey rh9128, around 14 months post transplantation 4 docetaxel doses were given of 10 mg/m$^2$. The appropriate amount of docetaxel was diluted in 50 ml PBS-Glucose (NPPI, The Netherlands) and was administered by IV injection at a rate of 1 ml/min.

Bone Marrow Processing and Transduction 40 ml of bone marrow aspirate was obtained by puncturing both femoral shafts under total anesthesia. Bone marrow cells were collected in Hanks' basic salt solution containing heparin at 100 units per ml and deoxyribonuclease-I and subjected to Ficoll-Hypaque (Sigma) cenitrifugation. CD34$^+$ selection was performed using a smallscale CEPRATE LC column (CellPro, Bothell, Wash.). From $5 \times 10^4$ to $50 \times 10^4$ cells were incubated at 4° C. for 30 min in 0.1 ml PBS and 1% bovine serum albumin (BSA) with 5 ml of a phycoerythrin-conjugated anti-CD34 antibody (563.F) or unconjugated anti-CD34 antibody (566). Cells incubated with the antibody 566 were washed (PBS, 0.1* BSA) and further incubated with PerCP conjugated Rabbit anti-Mouse IgG1 (Becton-Dickinson, Cat no. 340272). After washing, cells were acquired on a FACSort (Becton-Dickinson) flow cytometer. Cells were analyzed with the Lysis II software program. The percentage of CD34$^+$ cells was calculated as the ratio of CD34$^+$ cells to total number of cells and multiplied by 100. For rhesus monkeys 9128 and 9170, the enriched CD34+ cells were immediately processed for transduction. For rhesus monkeys A94 and BB94 the enriched CD34+ cells were split into two equal fractions and stored in liquid nitrogen.

Transduction of CD34+ cells was done as described below. A summary of the experimental conditions is given in table 3.

Rhesus monkey 9129 and 9170: Four days prior to transplantation the CDS34+ enriched cells were split in two equal fractions and cultured at a density of $10^6$ cells per ml in low density BMC culture medium supplemented with recombinant rhesus monkey interleukin-3 (RhIL-3; Burger et al., 1990) as described in [57], On day 2 and day 3, one fraction of cultured CD34+ cells was exposed to the crude rAAV preparation of IG-CFT and the other fraction was exposed to a crude rAAV-preparation of IG-ΔMoNeo by adding an equal volume of virus preparation to the medium of the cultured CD34+ cells. After three to five hours, the cells were collected by centrifugation (7 min, 200 g) and resuspended into fresh RhIL-3 supplemented low density BMC culture medium in the same volume as the culture was started in. On day four, the cells were collected by centrifugation (7 min, 200 g) and resuspended in an equal volume of 0.9% NaCl and separately transplanted into autologous rhesus monkeys by IV injection.

Rhesus monkey A94 and BB94: Four days prior to transplantation, one fraction of the frozen CD34+ enriched cells was thawed and subsequently washed with Hanks Balanced Salt solution. Live cells were collected by Ficoll-Hypaque (Sigma) centrifugation and cultured at a density of $10^6$ cells per ml in Iscove's modified Eagles medium (IMDM, Gibco-BRL) supplemented with Fetal Calf's Serum (FCS, 10%) and recombinant rhesus monkey interleukin-3 (RhIL-3; Burger et al., 1990). On day 2 and day 3, cells were collected by centrifugation (7 min, 200 g) and resuspended in 10 to 200 µl of IMDM+10% FCS and RhIL-3 and subsequently exposed to a purified rAAV preparation of IG-CFT (Monkey A94) or IG-CFT* (Monkey B994). After two hours, the cells were washed with IMDM+ 10% FCS and reseeded in IMDM+10% FCS and Rh-IL-3. At day four, the cells were collected by centrifugation and suspended in 0.9% NaCl. Also, on day four, the other fraction of CD34+ cells was thawed and washed with Hanks Balanced Salt solution. Live cells were collected by Ficoll-Hypaque (Sigma) centrifugation, resuspended in 10 to 200 µl of IMDM+10% FCS and RhIL-3 and subsequently exposed to a purified rAAV-preparation of IG-CFT (Monkey BB94) or IG-CFT* (Monkey A94). After two hours, the cells were collected by centrifugation and suspended in 0.9% NaCl. After collection in NaCl (0.9%), the cells were separately transplanted into autologous irradiated rhesus monkeys by IV injection.

Parameter Evaluation

Daily observation of clinical signs. Weekly complete physical examination and determination of body weight. Blood chemistry analysis was performed before and after x-ray irradiation. Hematology was performed weekly. Bone marrow samples were punctured from the femoral shafts under total anesthesia. Heparine blood samples were taken weekly for PCR analysis. PBMC and granulocytes were isolated from peripheral blood samples, as described previously by Ficoll Hypaque centrifugation (Van Seusechem et al., 1992). Circulating T- and B-cells were purified from PBMC by sorting CD2 and CD20 positive cells, respectively. FITC labeled CD2 (clone S 5.2; Becton-Dickinson, California) or CD20 (clone L27; Becton-Dickinson, California) antibodies were incubated with PBMC according to the manufacturers protocols. Labeled cells were separated using the MACS® column and anti-FITC beads (Miltenyi, Germany) according to the manufacturers protocol. Re-analyses of the sorted cells on FACS® (Becton-Dickinson, USA) showed that the sorted cells were more then 95% pure populations.

Colony-Forming Cell (CFU-C) Assay

Rh912B and Rh9170 hemopoietic cells were plated in duplicate at $5\times10^3$/ml (CD34+ selected) or $1\times10^5$/ml (post-Ficoll) in 1 ml methylcellulose medium, as described in [57], supplemented with 30 ng/ml rhIL-3 and 25 ng/ml GM-CSF. Rh A94 and BB94 hemopoietic cells were seeded for colony formation in methylcellulose medium containing 50 ng/ml SCF, 10 ng/ml GM-CSF, 10 ng/ml IL-3 and 3 U/ml Epo (MethoCult GF H4434, StemCell Technologies Inc, Vancouver, Canada).

Polymerase Chain Reaction

For cell lysis, pellets were incubated ($10^7$ cells/ml) in nonionic detergent lysis buffer (0.5% NP40, 0.5% Tween 20, 10 mM Tris pH 8.3, 50 mM KCl, 0.01% gelatin, 2.5 mM $MgCl_2$) containing proteinase K (60 mg/ml) at 56° C. for 1 hour, Lysates were then heated at 95° C. for 10 min to inactivate the proteinase K. Two different PCR detections were performed. One was a nested $neo^R$-specific PCR and one was a β-globin specific PCR. The protocol for the $neo^R$-specifiC PCR will be described first. The first amplification was performed on 10 µl lysates in a total volume of 50 µl with 2 U of SuperTaq polymerase (HT Biotechnology, Cambridge, England) in a reaction mix (final concentration: 200 mM each of 2'-deoxyadenosine-5'-triphosphate, 2'-deoxycytidine-5'-triphosphate, 2'-deoxyguanosine-5'-triphosphate, 2'-deoxythymidine-5'-triphosphate (Pharmacia, Roosendaal, The Netherlands), 0.2 µM each of 5' neo-1 and the antisense primer 3' neo-2 and the reaction buffer supplied by the manufacturer (HT Biotechnology, Cambridge, England). The nested amplification was performed on 5 µl of the first reaction in a total volume of 50 µl with 2 U of SuperTaq polymerase (HT Biotechnology, Cambridge, England) in a reaction mix (final concentration; 200 mM each of 2'-deoxyadenosine-5'-triphosphate, 2'-deoxycytidine-5'-triphosphate, 2'-deoxyguanosine-5'-triphosphate, 2'-deoxythymidine-5'-triphosphate (Pharmacia, Roosendaal, The Netherlands), 0.2 µM each of 5' neo-2 and the antisense primer 3' neo-1 and the reaction buffer supplied by the manufacturer (HT Biotechnology, Cambridge, England). Primers were chosen to selectively amplify the $neo^R$ gene.

The primer sequences are:

5' neo-1: 5'-GGGGTACCGCCGCCGCCACCATGATTG AACAAGATGGATTGC-3' (SEQ ID NO.1)

5' neo-2: 5'-TTCTCCGGCCGCTTGGGTGG-3' (SEQ ID NO.2)

3' neo-1: 5'-GGCAGGAGCAAGGTGAGATG-3' (SEQ ID NO.3)

3' neo-2: 5'-CCATGATGGATACTTTCTCG-3' (SEQ ID NO.4)

Amplification conditions were the same for the first and the nested amplification and were performed in a TRIO thermocycler (Biometra, Göttingen, Germany) temperature cycling apparatus, The conditions chosen were: 95° C. for 5 minutes, then 30 cycles of 94° C. for 30 seconds, 55° C. for 30 seconds, 72° C. for 1 minute, followed by extension at 72° C. for 10 minutes. Five to ten microliters of the nested reaction were separated on 2% agarose gel (Pronarose, Hispanagar, Burgos, Spain). Each assay included titrations of a murine erythroid leukemia cell line C88-C1, containing a single provirus integration of IG-CFT [21] and/or a titration of a pool of G418 selected MEL cells infected with IG-CFT*. For practical reasons, we developed an alternative PCR method to detect the neo-cassette in the rAAV-vectors IG-CFT, IG-CFT* and IG-ΔMo+NEO. The sequences of the primers were as follows; NEO-1S: 5'-TAGCGTTGGCTACCCGTGAT-3' (SEQ ID NO5), and NEO-4AS: 5'-TGCCGTCATAGCGCGGGTT-3' (SEQ ID NO.6). Reaction mixtures were prepared as described above and the reaction temperature was 95° C. for 3 minutes followed by 30 cycles of 95° C. for 30 seconds, 65° C. for 30 seconds and 72° C. for 1 minute. The completion of the 30 cycles was followed by an extension of 5 minutes at 72° C. Five to ten microliter of the PCR-reaction was run on a 2% agarose gel, blotted and hybridized to a 157 bp. specific probe isolated from a BstBI-SmaI digest of IG-CFT.

The β-globin specific PCR was carried out in essentially the same way as the first reaction of the $neo^R$-specific PCR. But instead of the $neo^R$-primers, the primers listed below, specific.for the 3' part of the HS-2 fragment and β-globin intron I, were added. The sequences of the primers are:

HS-2-S3 5'-GGAATTATTCGGATCTATCGAT-3' (SEQ ID NO.7)

IVS-1A-A 5'-TCCTTAAACCTGTCTTGTAACC-3' (SEQ ID NO.8)

The temperatures for the cycling were: 95° C. for 3 minutes and then 30 cycles of 95° C. for 30 seconds, 55° C. for 30 seconds, 72° C. for 30 seconds. Following the 30 cycles, an extension at 72° C. for 5 minutes was performed. Samples were run on 2% agarose gels, which were blotted and hybridized to a NcoI-ClaI β-globin promoter specific probe using standard techniques.

Hemopoietic Data of the Transplantation of Rhesus Monkeys with rAAV-Transduced BMC The survival and the selection of the purification and transduction procedure of $CD34^+$ rhesus monkey bone marrow cells was controlled by determining the number of CFU-C present at different stages in the procedure. The CD34 selection for Rh9128 and Rh9170resulted in a 13–19 fold enrichment of CFU-C resp. For A94 and BB94, the enrichment for CFU-C was 37–92 fold resp. (table 4). The number of CFU-C did not vary by more then a factor of 2 during culture or upon transduction, with the exception of monkey BB94 where the decrease in the number of CFU-C was considerable upon culture and infection with IG-CFT. This was due to a direct toxicity of the CsCl purified IG-CFT batch, as determined by a titration of the batch on human cord blood post ficoll bone marrow which resulted in a dilution factor dependent toxicity on CFU-C (not shown). Since it is known that CsCl is a very toxic substance, we determined the CsCl concentration in the two Cscl purified rAAV preparations. Both contained considerable amounts of CsCl, enough to account for the observed toxicity (table 2). Due to the observed toxicity on CFU-C in this experiment the two grafts that Rh-BB94 received were very different in size. Whereas the cultured graft wasostill considerable, the graft-size for the short transduction protocol was very small (table 4). However, since stem cells are not measured in a CFU-C assay and are indeed more resistant to a large variety of drugs and agents, it is possible that many of them survived the high concentration of CsCl.

Detection of rAAV Transduced Peripheral Blood Cells

To determine whether the engrafted cells had been transduced by the recombinant AAV vectors, approx. 3 ml of blood was collected each week from every monkey. Granulocytes and mononuclear cells were purified, as described in (57), and the DNA was released and analyzed by PCR for the presence of rAAV-sequences. Two different PCR reactions-were performed. On the samples from all four monkeys, PCR reactions specific for the $neo^R$-gene were performed. The $neo^R$-gene is present in all the vectors, so this PCR detects all recombinant AAV-genomes present in the cells. On the samples from monkeys rh-A94 and rh-BB94, also a β-globin specific PCR was performed. This PCR utilizes the size difference in the β-globin promoter in vectors IG-CFT and IG-CFT*. These vectors were used to transduce the P-PHSC via two different protocols, The effect of the two different protocols can thus be read out by the prevalence of one of the two vectors in the peripheral blood cells of the monkeys.

The results of the neo-PCR are depicted in FIGS. 2 and 3. All monkeys were negative for rAAV before transplantation and became positive for rAAV after transplantation. The presence of the vector varied from week to week. Some samples were positive for the vector, others were negative, indicating that the frequency of transduced cells averaged around the detection limit of the PCR-reaction which was determined to be at 1 copy in $10^5$ nucleated cells for the neo-specific PCR. Monkey BB94 was positive in all samples immediately after transplantation and regeneration of the hemopoietic system, indicating a more efficient transduction of early progenitors during the ex vivo handling of the cells.

In monkeys BB94 and 9128, vector containing cells could be detected for at least more then one year after transplantation. Bone marrow samples taken from these animals at 2 and 6 months (9128) or 14 months (BB94) post transplantation also contained vector transduced cells. In BB94, the vector was detected in PBMC, granulocytes, bone marrow and purified populations of B- and T-cells (FIG. 4). This result demonstrated the transduction of stem cells which had repopulated both the myeloid lineage (granulocytes) and the lymphoid lineage (T- and B-cells). The granulocytes, T cells, and B cells were still PCR positive more than 15 months post-transplantation, indicating the transduction of cells with extensive self-renewal capacity, The transduction of primate cells with (1) an extremely long-term in vivo stability after transplantation, and (2) the capability of multiple-lineage repopulation long after transplantation, provides strong evidence for transduction of P-PHSC.

Rhesus monkey 9128 received treatments with taxotere, a cytostatic drug, to ablate the mature cells in the circulation, inducing periodic regrowth from immature hemopoietic cells residing in the bone marrow. Recombinant AAV transduced cells were detected in circulating cells fter a series of treatments with taxotere, over a period of 14 months post transplantation. The persistence of transduced cells in peripheral blood cells and the resistance to taxotere treatment provides convincing evidence of the transduction of P-PHSC.

Determination of Most Efficient Transduction Protocol

The experiment with monkeys BB94 and A94 was designed to quantify the success of two different transduction protocols. For each monkey, the transplant was split in two equal fractions and each fraction was transduced in a different way. To be able to discriminate which protocol resulted in a better transduction, we used a different vector for each transduction. We compared the efficiency of transduction of cultured P-PHSC versus that of non-cultured P-PHSC. For the transduction of P-PHSC from monkey BB94, we used the purified virus IG-GFT for the non-cultured P-PHSC and the purified virus IG-CFT* for the cultured P-PHSC. To exclude a possible role of quality differences between the virus batches, we switched the two virus batches for the transduction protocols for monkey A94; we used IG-GFT for its cultured P-PHSC and IG-GFT* for its non-cultured P-PHSC. Following transplantation and repopulation of the. hemopoietic system of the monkeys, we performed the β-globin specific PCR to determine which transduction procedure resulted in the highest frequency of gene modified circulating cells. For both monkeys, we were able to detect only the virus used to transduce the cultured P-PHSC, i.e., IG-GFT* for monkey BB94 and IG-GFT for monkey A94 (FIG. 5). Thus, in vitro stimulation of P-PHSC results in a more efficient transduction with recombinant AAV vectors. This result was not expected. It is generally accepted that culture of P-PHSC promotes progressive loss of the grafting potential of the P-PHSC, presumably due to differentiation. Hence, if both procedures resulted in similar P-PHSC transduction efficiencies, we would expect the progeny of the non-cultured P-PHSC co prevail among the circulating blood cells due to grafting advantages. Since we observed the opposite, the stable transduction efficiency of the cultured P-PHSC must be significantly higher than that of the noncultured P-PHSC. It is known that AAV-vectors integrate with higher efficiency in cycling cells then in non-cycling cells (38) However, in non-cycling cells the vector remains in the nucleus and retains its ability to integrate when the cell is triggered into cycle (60). Once transplanted, the P-PHSC start to divide and repopulate the ablated hemopoietic system. Considering the enormous amount of cells that need to be produced in a short time, it is presumed that the P-PHSC start to divide within a couple of days once inside the body. Therefore, a difference in transducibility of cultured versus non-cultured cells is not expected when only replication of the target cells is the enhancing factor. We infer that culture and exposure to hemopoietic growth factors such as IL-3 could in other ways potentiate the transduction with recombinant AAV. One possible explanation is the up-regulation or activation of receptors for the virus on the surface of the P-PHSC. Another is the induction of proteins inside the P-PHSC that enhance for instance nuclear transport and/or other rate limiting steps for stable transduction.

Literature

1. Einerhand M P W, Valerio D: Gene transfer into hematopoietic stem cells: prospects for human gene therapy, in Muller-Sieberg C, Visser J W M, Torock-Storb B, Storb R (eds): Stem cells in hematopoiesis: Animal models and human transplantation. Curr. Top. in Microbiol. and Immunol., Berlin-Heidelberg, Springer-Verlag GmbH & Co KG, 1992, p. 217–235
2. Einerhand M P W, Bakx T A, Kukler A, Valerio D: Factors affecting the transduction of pluripotent hemopoietic stem cells: long term expression of a human adenosine deaminase gene in mice. Blood 81: 254–263, 1993
3. Van Beusachem V, Valerio D: Gene transfer into hematopoietic stem cells of non human primates. Hum. Gene Ther. 7: in press, 1996
4. Dunbar C, Cottler-Fox M, O'Shaughnessy J, Doren S, Carter C, Berenson R, Brown S, Moen R, Greenblatt J, Stewart F, Leitman S, Wilson W, Cowan K, Young N, Nienhuis A: Retrovirally marked CD34-enriched peripheral blood and bone marrow cells contribute to long-term engraftment after autologous transplantation. Blood 85: 3048–3057, 1995
5. Deisseroth A, Zu Z, Claxton D, Hanania E, Fu S, Ellerson D: Genetic marking shows that Ph+cells present in autologous transplants of chronic myelogenous leukemia (CML) contribute to relapse after autologous bone marrow in CML. Blood 83: 3068–3076, 1994
6. Brenner M K, Rill D R, Holladay M S, Heslop H E, Moen R C, Buschle M, Krance R A, Santana V M, Anderson W F, Ihle J N: Gene marking to determine whether autologous marrow infusion restores long-term haemopoiesis in cancer patients. Lancet 342: 1134–1137, 1993
7. Cornetta K, Srour E, Moore A, Davidson A, Broun E, Hromas A, R C M, Morgan R, Rubin L, Anderson W. Hoffman R, Tricot G: Retroviral gene transfer in autologous bone marrow transplantation for adult acute leukemia. Hum. Gene Ther. 7; 1323–1329, 1996
8. Fritsch E, Temin H: Inhibition of viral DNA synthesis in stationary chicken embryo fibroblasts infected with avian retroviruses. J. Virol. 24: 461–469, 1977
9. Harel J, Rassart E, Jolicoeur P; Cell cycle dependence 5 of synthesis of unintegrated DNA in mouse cells newly infected with murine leukemia virus. Virology 110: 202–207, 1981
10. Miller D G, Adam M A, Miller A D: Gene transfer by retrovirus vectors occurs only in cells that are actively replicating at the time of infection. Mol Cell Biol 10: 4239–4242, 1990
11. Springett G, Moen R, Anderson S, Blaese R, Anderson W: Infection efficiency of T lymphocytes with amphotropic retroviral vectors is cell cycle dependent. J. Virol. 63: 3865–3869, 1989
12. Berns K I, Rose J A: Evidence for a single-stranded adeno-associated virus genome; isolation and separation of complementary single strands. J. Virol. 5; 693–699, 1970
13. Berns K I, Adler S: Separation of two types of adeno-associated virus particles containing complementary polynucleotide chains. Virology 9: 394–396, 1972
14. Lusby E, Fife K H, Berns K I: Nucleotide sequence of the inverted terminal repetition in adeno-associated virus DNA. J. Virol. 34: 402–409, 1980
15. Samulski R J, Chang L, Shenk T: Helper-free stocks of recombinant adeno-associated viruses: normal integration does not require viral gene expression. J. Virol. 63: 3822–3828, 1969
16. Tratschin J D, Miller I L, Smith M G, Carter B J: Adeno-associated virus vector for high-frequency integration, expression, and rescue of genes in mammalian cells. Mol. Cell. Biol. 5; 3251–3260, 1985
17. Hermonat P L, Muzyczka N. Use of adeno-associated virus as a mammalian DNA cloning vector: transduction of neomycin resistance into mammalian tissue culture cells, Proc. Natl. Acad. Sci, USA 81; 6466–6470, 1984
18. McLaughlin S K, Collis P. Hermonat P L, Muzyczka N: Adeno-associated virus general transduction vectors: analysis of proviral structures. J. Virol. 62: 1963–1973, 1988
19. Lebkowski J S, McNally M M, Okarma T B, Lerch L B: Adeno-associated virus; a vector system for efficient introduction and integration of DNA into a variety of mammalian cell types. Mol. Cell. Biol. 8: 3988–3996, 1988
20. Walsh C E, Liu J M, Xiao X, Young N S, Nienhuis A W, Samulski R J: Regulated high level expression of a human γ-globin gene introduced into erythroid cells by an adeno-associated virus vector. Proc. Natl. Acad. Sci. USA 89: 7257–7261, 1992
21. Einerhand M, Antoniou M, Zolotukhin S, Muzyczka N, Berns K, Grosveld F, Valerio D: Regulated high-level β-globin gene expression in erythroid cells following recombinant adeno-associated virus-mediated gene transfer. Gene Ther. 2: 336–343, 1995
22. Collis P, Antoniou M, Grosveld F: Definition of the minimal requirements within the human β-globin gene and the dominant control region for high level expression. EMBO J. 9: 233–240, 1990
23. Mclvor R S, Johnson M J, Miller A D, Pitts S, Williams S R, Valerio D, Martin Jr. D W, Verma I M: Human purine nucleoside phosphorylase and adenosine deaminase: gene transfer into cultured cells and murine hematopoietic stem cells by using recombinant amphotropic retroviruses. Mol. Cell. Biol. 7: 839–846, 1987
24. Berns K I: Parvovirus replication. Microbiol. Rev. 54: 316–329, 1990
25. Kotin R M, Siniscalco M, Samulski R J, Zhu X, Hunter L, Laughlin S, Muzyczka N, Rocchi M, Berns K I: Site-specific integration by adeno-associated virus. Proc. Natl. Acad. Sci. USA 87: 2211–2215, 1990
26. Samulski R J, Zhu X, Xiao X, Brook J D, Housman D E, Epstein N. Hunter L A: Targeted integration of adeno-associated virus (AAV) into human chromosotne 19. EMBO J. 10: 3941–3950, 1991
27. Chiorini J A, Weitzman M D, Owens R A, Urcelay E, Safer B, Kotin R M: Biologically active rep proteins of adeno-associated virus type 2 produced as fusion proteins in *Escherichia coli*. J. Virol. 68: 797–804, 1994
28. Berns K I: Parvoviridae and their replication, in Chanock R M, Hirsch M S, Melnick J L, Monath T P, Roizman B (eds): Virology, New York, Raven Press, 1990, p. 1743–1763
29. Flotte T R, Solow R, Owens R A, Afione S, Zeitlin P L, Carter E J: Gene expression from adeno-associated virus vectors in airway epithelial cells. Am. J. Respir. Cell Mol. Biol. 7: 349–356, 1992
30. Flotte T R, Afione S A, Conrad C, McGrath S A, Solow R, Oka H, Zeitlin P L, Gugginoa W B, Carter B J: Stable in vivo expression of the cystic fibrosis transmembrane conductance regulator with an adeno-associated virus vector. Proc. Natl. Acad. Sci. USA 90: 10613-1-617, 1993
31. Egan M, Flotte T, Afione S. Solow R, Zeitlin P L, Carter B J, Guggino W B: Defective regulation of outwardly rectifying Cl- channels by protein kinase A corrected by insertion of CFTR. Nature 358: 581–584, 1992
32. LaPace D, Hermonat P, Wakeland E, Peck A: Gene transfer into hemopoietic progenitor cells mediated by an adeno-associated virus vector. Virol. 162: 483–486, 1988
33. Zhou S Z, Broxmeyer H E, Cooper S, Harrington M A, Srivastava A: Adeno-associated virus 2-mediated gene transfer into murine hematopoietic progenitor cells. Exp Hematol. 21: 928–933, 1993
34. Zhou S Z, Cooper S. Kang L Y, Ruggierri L, Heimfeld S, Srivastava A, Broxineyer H E: Adeno-associated virus 2-mediated high efficiency gene transfer into immiature and mature subsets of hematopoietic progenitor cells in human ukmbilical cord blood. J. Exp. Med. 179: 1867–1875, 1994
35 Goodman S, Xiao X, Donahue R E, Moulton A, Miller J, Walsh C, Young N S, Samulski R J, Nienhuis A W: Recombinant adeno-associated virus-mediated gene transfer into hematopoietic progenitor cells. Blood B4: 1492–1500, 1994
36. Chatteryee S, Johnson P R, Wong K K: Dual-target inhibition of HIV-1 in vitro by means of an adeno-associated virus antisense vector. Science 258: 1485–1488, 1992
37. Luhovy M, McCune S, Dong J Y, Prchal J F, Townes T M, Prchal J T: Stable transduction of recombinant adeno-associated virus into hematopoietic stem cells from normal and sickle cell patients. Biol. of Blood and Marrow Transpl. 2; 24–30, 1996
38. Russell D W, Miller A D, Alexander I E; Adeno-associated virus vectors preferentially transduce cells in S phase. Proc. Natl. Acad. Sci. USA 91; 8915–8919, 1994
39. Wintrobe M M, Lee G R, Boggs D R, Bithell T C, Foerster J, Athens J W, Lukens J N: Glinical hematology: 869–903, 1981
40. Rodgers G P, Dover G J, Noguchi C T, Schlechter A N: Hematologic responses of patients with sickle cell disease to treatment with hydroxyurea. N. Engl. J. Med. 322; 1037–1045, 1990
41. Anderson W F: Prospects for human gene therapy. Science 226: 401–409, 1984
42. Evans T, Felsenfeld G, Reitman M: Control of globin gene transcription. Ann. Rev. Cell Biol. 6: 95–124, 1990
43. Grosveld F. Blom van Assendelft G, Greaves D R, Kollias G: Position-independent, high-level expression of the human β-globin gene in transgenic mice. Cell 51: 975–985, 1987
44. Talbot D, Collis P, Antoniou M, Vidal M, Grosveld F, Greaves D R: A dominant control region from the human β-globin locus conferring integration site independent gene expression. Nature 338: 352–355, 1989
45. Miller J L, Walsh C E, Ney P A, Samulski R J, Nienhuis A W: Single-copy transduction and expression of human γ-globin in K562 erythroleukemia cells using recombinant adeno-associated virus vectors: the effect of mutations in NF-E2 and GATA-1 binding motifs within the hypersensitivity site 2 enhancer, Blood 82: 1900–1906, 1993
46. Einerhand M P W, Valerio D: Viral vector systetns tor bone marrow gene therapy, in Levitt, Mertelsmann (eds): Hematopoietic Stem Cells; Biology and therapeutic applications, New York, Marcel Dekker, inc, 1995, p 275–295
47. Halbert C L, Alexander I E, Wolgamot G M, Miller A D: Adeno-associated virus vectors transduce primary cells much less efficient than immortalized cells. J. Virol. 69: 1473–1479, 1995
48. Ferrari F K, Samulski T, Shenk T, Samulski R J: Second strand synthesis is a rate limiting step for efficient transduction by recombinant adeno-associated virus vectors. J. Virol. 70: 3227–3234, 1996
49. Nienhuis A: Gene Therapy for Hematopoietic Stem Cells in Genetic Disease and Cancer. Keystone Symposia on Molecular and Cellular Biology, Taos, N. Mex. Peb. 4–10, 1996
50, Lefebvre R B, Riva S, Berns K I: Conformation takes precedence over sequence in adeno-associated virus DNA replication, Mol. Cell Biol. 4: 1416–1419, 1984
51. Van Beusechem V W, Kukler A, Einerhand M P W, Bakx T A, Van der Eb A J, Van Bekkum D W, Valerio D: Expression of human adenosine deaminase in mice transplanted with hemopoietic stem cells infected with amphotropic retroviruses. J. Exp. Med. 172: 729–736, 1990
52. Valerio D, Einerhand M P W, Wamsley P M, Bakx T A, Li C L, Verma I M: Retrovirus-mediated gene transfer into eibryonal carcinoma cells and hemopoietic stem cells: Expression from a hybrid long terminal repeat. Gene 84: 419–427, 1989
53. Linney E, Davis B, Overhauser J, Chao E, Fan H: Non-function of a Moloney Murine Leukemia Virus regulatory sequence in F9 embryonal carcinoma cells. Nature 308; 470–472, 1984
54. McKnight S: The Nuceotide sequence and transcript map of the herpes simplex thymidine kinase gene. Nucl. Acids Res. 8: 5949–5964, 1980
55. Graham F L, Smiley J, Russell W C, Naiva R: Characteristics of a human cell line transformed by DNA from aderiovirus type 5. J. Gen. Virol. 36: 59–72, 1977
56. Deisseroth A, Hendrick D: Human β-globin gene expression following chromosomal dependent gene transfer into mouse erythroleukemia cells. Cell 15: 55–63, 1978

57. Van Beusechem V W, Kukler A, Heidt P J, Valerio D: Long-term expression of human adenosine deaminase in rhesus monkeys transplanted with retrovirus-infected bone-marrow cells. Proc. Natl, Acad. Sci. USA 89: 7640–7644, 1992
58. Thomson B J, Weindler F W, Gray D, Schwaab V, Heilbronn: Human Herpesvirus 6 (HHV-6) is a helpervirus for adeno-associated virus type 2 (AAV-2) and the AAV-2 rep gene homologue in HHV-6 can mediate AAV-2 DNA replication and regulate gene expression. Virol. 204: 304–411, 1994
59. Fischer-Adams G, Wong JR K K, Podsakoff G, Forman S J, Chatterjee S: Integration of Adeno-associated virus vectors in CD34+ human hemopoietic progenitor cells after transduction. Blood 88: 492–504, 1996
60. Podsakoff G, Wong JR K K, Chatterjee S: Efficient gene transfer into nondividing cells by adeno-associated virus-based vectors. J Virol 68: 5656–5666, 1994

TABLE 1

| | AAV | Amphotropic Retrovirus |
|---|---|---|
| Vector design | | |
| Maximum insert size | 4.5 kb | 8 kb |
| Intron compatible | Yes | Poor |
| Vector transcription in packaging cell | Not required | Should be high |
| Hemopoietic host range | | |
| Murine in vitro CFU | Yes[a] | Yes[b] |
| Murine PHSC | Not yet reported | Yes[c] |
| Human in vitro CD34+ CFU | Yes[d] | Yes[e] |
| Human in vivo longlived progenitors | Not yet reported | Yes[f] |
| Provirus integrity | | |
| Point mutations per viral genome* | 0.005 | 1 |
| Recombination frequency | Insert-dependent | Insert-dependent |
| Virus production | | |
| Crude titers | $10^{5}$ [g] | $10^{7}$ [h] |
| Concentrated titers | $10^{10}$ [i] | $10^{8}$ [j] |
| Helper free stocks | Yes | Yes |

Properties of adeno-associated virus and amphotropic retrovirus vectors. *Calculated number per replication cycle. AAV is replicated via cellular DNA-polymerases which have proof reading activity. The error frequency of these polymerases is $10^{-6}$ implying 1 point mutation per 200 recombinant AAV genomes. Retroviruses are replicated via RNA-polymerase II and reverse transcriptase (RT). The known error frequency of RT is $10^{-4}$. Not much is known about the mutation rate of RNA-polymerase II. Based on the error frequency of RT one can expect one point mutation per retroviral genome of 10 kb. [a][Srivastava, 1993]; [b][Joyner, 1983]; [c][Einerhand, 1992 #109 ]; [d][Chatteryee, 1992]; [e][Nolta, 1992]; [f][Brenner, 1993]; [g][Walsh, 1992]; [h][Miller, 1992]; [i][Flotte, 1993]; [j][Kotani, 1994; Lynch, 1991].

TABLE 2

| rAAV vector | Purification | Infectious Particles (IP/ml) | Transducing Particles (TP/ml) | wtAAV titer (IP/ml) | Adenovirus ts149 pfu/ml | CsCl (mg/ml) |
|---|---|---|---|---|---|---|
| IG-CFT | Crude | $2 \times 10^{6}$ | $10^{4}$ | $4.5 \times 10^{4}$ | $<10^{4}$ | N.D. |
| IG-ΔMo-Neo | Crude | $2 \times 10^{7}$ | $10^{3}$ | $<10^{3}$ | N.D. | N.D. |
| IG-CFT | CsCl | $10^{9}$ | $3.3 \times 10^{5}$ | $10^{9}$ | $<10^{4}$ | 64 |
| IG-CFT* | CsCl | $3 \times 10^{8}$ | $3.3 \times 10^{4}$ | $3 \times 10^{9}$ | $<10^{4}$ | 44 |

TABLE 3

| Rhesus monkey | rAAV-vector | Virus stock | Time in culture | CD34+ Cells | no. of IP | no. of TP | IP/Cell | TP/Cell |
|---|---|---|---|---|---|---|---|---|
| 9170 | IG-ΔMo-Neo | Crude | 4 | $5 \times 10^{6}$ | $10^{7}$ | 500 | 20 | $10^{-3}$ |
| | IG-CFT | Crude | 4 | $5 \times 10^{6}$ | $10^{6}$ | 500 | 2 | $10^{-2}$ |
| 9128 | IG-ΔMo-Neo | Crude | 4 | $9 \times 10^{5}$ | $10^{7}$ | 500 | 20 | $10^{-3}$ |
| | IG-CFT | Crude | 4 | $9 \times 10^{5}$ | $10^{6}$ | 500 | 2 | $10^{-2}$ |
| BB94 | IG-CFT* | CsCl | 4 | $4 \times 10^{6}$ | $2 \times 10^{7}$ | $2 \times 10^{3}$ | 5 | $5 \times 10^{-4}$ |
| | IG-CFT | CsCl | 0 | $2 \times 10^{6}$ | $1 \times 10^{8}$ | $3.3 \times 10^{4}$ | 50 | $2 \times 10^{-2}$ |
| A94 | IG-CFT | CsCl | 4 | $6 \times 10^{5}$ | $1.3 \times 10^{6}$ | 430 | 2 | $4 \times 10^{-4}$ |
| | IG-CFT* | CsCl | 0 | $2 \times 10^{5}$ | $1.5 \times 10^{6}$ | 160 | 7.5 | $8 \times 10^{-4}$ |

TABLE 4

| Rhesus monkey | rAAV-vector | Virus stock | Time in culture (days) | CD34+ Cells (×10⁵) | CFU-C per $10^{5}$ Cells | Graft-size in CFU-C (×$10^{3}$) | Reticulocyte regeneration date |
|---|---|---|---|---|---|---|---|
| 9170 | — | — | 0 | 100 | 1520 | | |
| | IG-ΔMo-Neo | Crude | 4 | 50 | 1480 | 74 | |
| | IG-CFT | Crude | 4 | 50 | 900 | 45 | 22 |
| 9128 | — | — | 0 | 18 | 940 | | |
| | IG-ΔMo-Neo | Crude | 4 | 9 | 1860 | 16 | |
| | IG-CFT | Crude | 4 | 9 | 1400 | 12 | 24 |
| BB94 | — | — | 0 | 40 | 12000 | | |
| | IG-CFT* | CsCl | 4 | 40 | 2000 | 75 | |
| | — | — | 0 | 20 | 16000 | | |
| | IG-CFT | CsCl | 0 | 20 | 80 | 1.5 | 22 |

TABLE 4-continued

| Rhesus monkey | rAAV-vector | Virus stock | Time in culture (days) | CD34+ Cells ($\times 10^5$) | CFU-C per $10^5$ Cells | Graft-size in CFU-C ($\times 10^3$) | Reticulocyte regeneration date |
|---|---|---|---|---|---|---|---|
| A94 | — | — | 0 | 6 | 12 | | |
| | IG-CFT | CsCl | 4 | 6 | 23 | 130 | |
| | — | — | 0 | 2 | 21 | | |
| | IG-CFT* | CsCl | 0 | 2 | 17 | 34 | 25 |

What is claimed is:

1. A process of genetically modifying pluripotent hemopoietic stem cells of primates (P-PHSC), said process comprising:
   harvesting P-PHSC:
   after said harvesting, culturing said harvested P-PHSC in a culture medium allowing for proliferation of said P-PHSC; and
   after said culturing, introducing a recombinant adeno-associated virus (AAV) vector into said cultured P-PHSC to genetically modify said cultured P-PHSC.

2. The process of claim 1, wherein the recombinant AAV vector is derived from human AAV.

3. The process of claim 2, wherein the recombinant AAV vector comprises a DNA sequence flanked by AAV inverted terminal repeats (ITR) or by mutant or recombinant ITR sequences that function as an AAV ITR or by fragments of any thereof that function as an ITR.

4. The process of claim 3, wherein said DNA sequence comprises regulatory sequences which are functional in hemopoietic cells and, under control of said regulatory sequences, a sequence coding for a protein or RNA with a therapeutic property when introduced into hemopoietic cells.

5. The process of claim 4, wherein said DNA sequence comprises a coding sequence of a gene selected from a group consisting of a human lysosomal glucocerebrosidase gene (E.C.3.2.1.45), a globin gene from a human β-globin gene cluster, a DNA sequence encoding an RNA or protein with anti-viral activity, an α1-antitrypsin gene and a human multidrug resistance gene I (MDRI).

6. The process of claim 5, wherein said DNA sequence comprises the human β-globin gene inclusive of at least one intron.

7. The process of claim 6, wherein said DNA sequence comprises the human β-globin gene operably linked to erythroid-specific DNaseI hypersensitive sites from its Locus Control Region (LCR).

8. The process of claim 7, wherein said erythroid-specific DNaseI hypersensitive sites from β-globin LCR comprise β-LCR elements HS4, HS3 and HS2.

9. The process of claim 8, wherein said DNA sequence comprises the human β-globin gene under transcriptional control of a functional part of a β-globin promoter.

10. The process of claim 9, wherein said DNA sequence comprises a selectable marker gene useful in hemopoietic stem cells.

11. The process of claim 10, wherein said selectable marker gene is a neo$^R$ gene under transcriptional control of a herpes simplex virus (HSV) thymidine kinase (tk) promoter.

12. The process of claim 10, wherein said selectable marker gene is a neo$^R$ gene under transcriptional control of a ΔMo+PyF101 Long Terminal Repeat (LTR) promoter.

13. The process of claim 11, wherein said recombinant AAV vector is part of a complex when contacted with said P-PHSC.

14. The process of claim 12, wherein said recombinant AAV vector is part of a complex when contacted with said P-PHSC.

15. The process of claim 13, wherein said recombinant AAV vector is associated with AAV capsid proteins.

16. The process of claim 13, wherein said recombinant ector is packaged into an AAV capsid.

17. The process of claim 14, wherein said recombinant AAV vector is associated with AAV capsid proteins.

18. The process of claim 16, wherein said recombinant AAV vector is introduced into said P-PHSC by transduction with the recombinant AAV vector packaged in an AAV capsid.

19. The process of claim 17, wherein said recombinant AAV vector is packaged into an AAV capsid.

20. The process of claim 18, wherein said P-PHSC are obtained from primate bone marrow, cord blood or peripheral blood.

21. The process of claim 19, wherein said recombinant AAV vector is introduced into said P-PHSC by transduction with the recombinant AAV vector packaged in an AAV capsid.

22. The process of claim 20, wherein said P-PHSC are obtained from a human.

23. The process of claim 21 wherein said P-PHSC are obtained from primate bone marrow, cord blood or peripheral blood.

24. The process of claim 22, wherein said P-PHSC are exposed in vitro to one or more proliferation stimulating compounds.

25. The process of claim 23, wherein said P-PHSC are obtained from a human.

26. The process of claim 24, wherein said P-PHSC are exposed in vitro to interleukin 3 or a fragment thereof.

27. The process of claim 25 wherein said P-PHSC are exposed in vitro to one or more proliferation stimulating compounds.

28. The process of claim 27, wherein said P-PHSC are exposed in vitro to interleukin 3 or a fragment thereof.

* * * * *

UNITED STATES PATENT AND TRADEMARK OFFICE
CERTIFICATE OF CORRECTION

PATENT NO.    : 6,312,957 B1
DATED         : November 6, 2001
INVENTOR(S)   : Markus Peter Wilhemus Einerhand and Domineco Valerio It is certified that error appears in the above-identified patent and that said Letters Patent is hereby corrected as shown below:

Title page,
Item [57], ABSTRACT,
Line 3, change "Tile Genomc" to -- The Genome --
Line 7, change "hemopoictic" to -- hemopoietic --
Line 11, change "glococerebrosidase" to -- glucocerebrosidase --

Column 1,
Line 54, change "P-PUSC" to -- P-PHSC --

Column 2,
Line 42, change "such" to -- Such --

Column 3,
Line 7, change "speciftc" to -- specific --
Line 17, change "inTmunogenicity" to -- immunogenecity --
Line 38, change "neon" to -- $neo^R$ --
Line 65, change "CVTR" to -- CFTR --

Column 5,
Line 12, change "humans, tInorporation" to -- humans. Incorporation --
Line 40, change "sequence," to -- sequence. --
Line 47, change "the." to -- the --
Line 48, change "genee" to -- genes --

Column 6,
Line 16, change "ability," to -- ability. --
Line 65, change "use," to -- use. --

Column 7,
Line 7, change "embodiment" to -- embodiment, --
Line 43, change "rAAV," to -- rAAV. --
Line 57, change "transtections" to -- transfections --

Column 8,
Line 32, change "hemopoiatic" to -- hemopoietic --
Line 61, change "repeat," to -- repeat.--

Column 9,
Line 4, change "BgIII" to -- BglII --

UNITED STATES PATENT AND TRADEMARK OFFICE
CERTIFICATE OF CORRECTION

PATENT NO.    : 6,312,957 B1
DATED         : November 6, 2001
INVENTOR(S)   : Markus Peter Wilhemus Einerhand and Domineco Valerio It is certified that error appears in the above-identified patent and that said Letters Patent is hereby corrected as shown below:

<u>Column 10,</u>
Line 22, change "Ads" to -- Ad5 --
Line 36, change "pBluescript," to -- pBluescript.--

<u>Column 11,</u>
Line 31, change "(1,5 M" to -- (1.5 M --
Line 63, change "PCA" to -- RCA --

<u>Column 12,</u>
Line 29, change "indicationl,and" to -- indication and --
Line 33, change "Salmionella" to -- Salmonella --
Line 34, change "septis" to -- sepsis --

<u>Column 13,</u>
Line 10, change "CDS34$^+$" to -- CD34$^+$ --
Line 14, change "(57)," to -- (57). --
Line 40, change "B994" to -- BB94 --
Line 58, change "x-ray" to -- X-ray --
Line 63, change "Seusechem" to -- Beusechem --

<u>Column 14,</u>
Line 23, change "hour," to -- hour. --
Line 27, change "specifiC" to -- specific --

<u>Column 15,</u>
Line 21, change "specific.for" to -- specific for --
Line 40, change "Rh9170resulted" to -- RH9170 resulted --
Line 57, change "wasostill" to -- was still --

<u>Column 16,</u>
Line 2, change "reactions-" to -- reactions --
Line 11, change "protocols," to -- protocols. --
Line 39, change "capacity," to -- capacity. --

<u>Column 17,</u>
Line 4, change "the." to -- the --
Line 17, change "co" to -- to --

UNITED STATES PATENT AND TRADEMARK OFFICE
CERTIFICATE OF CORRECTION

PATENT NO. : 6,312,957 B1
DATED : November 6, 2001
INVENTOR(S) : Markus Peter Wilhemus Einerhand and Domineco Valerio It is certified that error appears in the above-identified patent and that said Letters Patent is hereby corrected as shown below:

Column 18,
Line 14, after "dependence" delete "5"
Line 39, change "1969" to -- 1989 --
Line 53, change "virus;" to -- virus: --

Column 19,
Line 17, change "chromosotne" to -- chromosome --
Line 32, change "Gugginoa" to -- Guggino --
Line 40, change "LaPace" to -- LaFace --
Line 49, change "immiature" to -- immature --
Line 51, change "ukmbilical" to -- umbilical --
Line 53, change "35" to -- 35. --
Line 56, change "B4" to -- 84 --

Column 20,
Line 27, change "systetns tor" to -- systems for --
Line 29, change "Cells;" to -- Cells: --
Line 42, change "Peb." to -- Feb. --
Line 44, change "50," to -- 50. --
Line 46, change "replication," to -- replication. --
Line 54, change "eibryonal" to -- embryonal --
Line 66, change "aderiovirus" to --adenovirus --

Column 26,
Line 64, change "introducedinto" to -- introduced into --

UNITED STATES PATENT AND TRADEMARK OFFICE
CERTIFICATE OF CORRECTION

PATENT NO. : 6,312,957 B1
DATED : November 6, 2001
INVENTOR(S) : Markus Peter Wilhemus Einerhand and Domineco Valerio It is certified that error appears in the above-identified patent and that said Letters Patent is hereby corrected as shown below:

<u>Column 28,</u>
Line 2, change "ector" to -- AAV vector --

Signed and Sealed this

Twentieth Day of May, 2003

JAMES E. ROGAN
*Director of the United States Patent and Trademark Office*